United States Patent
Davies et al.

(10) Patent No.: US 8,729,274 B2
(45) Date of Patent: May 20, 2014

(54) TRICYCLIC HETEROCYCLIC DERIVATIVES

(75) Inventors: Keneth Davies, West Lothian (GB); Takao Kiyoi, Lanarkshire (GB); Ashvinkumar Dhirubhai Mistry, Newhouse (GB); Peter Christopher Ray, Newhouse (GB); Mark Reid, West Lothian (GB); Grant Wishart, Lanarkshire (GB)

(73) Assignee: Merck Sharp & Dohme B.V., Haarlem (NL)

( * ) Notice: Subject to any disclaimer, the term of this patent is extended or adjusted under 35 U.S.C. 154(b) by 221 days.

(21) Appl. No.: 13/255,630

(22) PCT Filed: Mar. 9, 2010

(86) PCT No.: PCT/EP2010/052976
§ 371 (c)(1),
(2), (4) Date: May 8, 2012

(87) PCT Pub. No.: WO2010/103001
PCT Pub. Date: Sep. 16, 2010

(65) Prior Publication Data
US 2012/0232122 A1    Sep. 13, 2012

(30) Foreign Application Priority Data

Mar. 10, 2009    (EP) .................................... 09154796

(51) Int. Cl.
*C07D 209/62*    (2006.01)
*A61K 31/403*    (2006.01)

(52) U.S. Cl.
USPC .......................................... 548/427; 514/411

(58) Field of Classification Search
None
See application file for complete search history.

(56) References Cited

U.S. PATENT DOCUMENTS

| | | | |
|---|---|---|---|
| 4,618,683 A | 10/1986 | DeBernardis et al. | |
| 4,622,405 A | 11/1986 | DeBernardis et al. | |
| 5,049,564 A | 9/1991 | DeBernardis et al. | |
| 5,244,888 A | 9/1993 | DeBernardis et al. | |

FOREIGN PATENT DOCUMENTS

| EP | 0 222 703 A1 | 5/1987 |
|---|---|---|
| EP | 0 461 353 A1 | 12/1991 |
| WO | 90/06927 A1 | 6/1990 |
| WO | 2007/081299 A2 | 7/2007 |
| WO | 2007/081299 A3 | 7/2007 |

OTHER PUBLICATIONS

Reimann et al. Arch. Pharm. (Weinheim) 319, 999-1009 (1986).*
Cannon, J. G. et al., "Congeners of the alpha Conformer of Dopamine Derived from Octahydrobenz[ h ]isoquinoline", J. Med. Chem., 1980, p. 502-505, vol. 23.
Dunlop, J. et al., "Pharmacological Profile of the 5-HT2c Receptor Agonist WAY-163909; Therapeutic Potential in Multiple Indications", CNS Drug Reviews, 2006, p. 167-177, vol. 12, No. 3-4.
Kametani, T. et al., "Reaction of 1,2-Dihydrobenzocyclobutene-1-carbonitriles with Methyl Acrylate as an Unsymmetric Dienophile", Perkin Transactions 1, 1975, p. 2001-2004, vol. 19.
Kim, K. H. et al., "Quantitative Structure-Activity Relationships for Substituted Aminotetralin Analogues. II: Inhibition of Dopamine Uptake", Journal of Pharmaceutical Sciences, 1993, p. 521-525, vol. 82, No. 5.
Kim, K. H. et al., "Quantitative Structure-Activity Relationships for Substituted Aminotetralin Analogues. I: Inhibition of Norepinephrine Uptake", Journal of Pharmaceutical Sciences, 1993, p. 355-361, vol. 82, No. 4.
Oppolzer, W., "Steric Control of Intramolecular Ortho-Quinodimethane-Cycloadditions", Tetrahedron Letters, 1974, p. 1001-1004, No. 12.
Siuciak, J. A. et al., "CP-809,101, a selective 5-HT2c agonist, shows activity in animal models of antipsychotic activity", Neuropharmacology, 2007, p. 279-290, vol. 52.
Wacker, D. A. et al., "Discovery of (R)-9-Ethyl-1,3,4,10b-tetrahydro-7trifluoromethylpyrazino[2,1-a]isoindol-6(2H)-one, a Selective, Orally Active Agonist of the 5-HT2C Receptor", J. Med. Chem, 2007, p. 1365-1379, vol. 50.

* cited by examiner

*Primary Examiner* — Nyeemah A Grazier
(74) *Attorney, Agent, or Firm* — Baerbel R. Brown; Catherine D. Fitch

(57) ABSTRACT

The present invention relates to a tricyclic heterocyclic derivative according to Formula (I), wherein the variables are defined as in the specification, or to a pharmaceutically acceptable salt or solvate thereof. The present invention also relates to pharmaceutical compositions comprising said tricyclic heterocyclic derivatives and to their use in therapy, for instance in the treatment or prevention of serotonin mediated disorders, such as obesity.

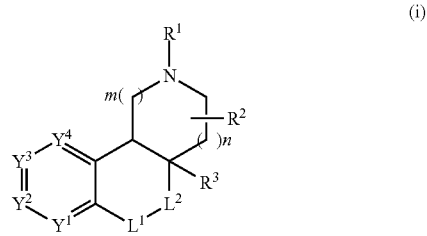

(i)

12 Claims, No Drawings

TRICYCLIC HETEROCYCLIC DERIVATIVES

CROSS REFERENCE TO RELATED APPLICATIONS

This application is the national stage application under 35 U.S.C. 371 of International Patent Application No.: PCT/EP2010/052976, filed in the U.S. Receiving Office on Mar. 9, 2010, which claims the benefit of European Application No. 09154796.8, filed Mar. 10, 2009. Each of the aforementioned PCT and Provisional applications is incorporated by reference in its entirety as if fully set forth herein.

The present invention relates to tricyclic heterocyclic derivatives, to pharmaceutical compositions comprising these compounds and to their use in therapy, in particular to their use for the treatment or prevention of serotonin mediated disorders, such as obesity.

The 5-hydroxytryptamine-2 (5-HT$_2$) receptors are a family of G-protein coupled receptors comprising three members (5-HT$_{2A}$, 5-HT$_{2B}$ and 5-HT$_{2C}$). 5-HT$_2$ subtypes activate the phospholipase C second messenger pathway, resulting in phosphoinositide hydrolysis and a transient increase in intracellular calcium. Certain 5-HT$_2$ subtypes can also activate the phospholipase A2 pathway, leading to release of arachidonic acid. The human 5-HT$_{2C}$ receptor was cloned in 1991 and unlike the 5-HT$_{2A}$ and 5-HT$_{2B}$ receptors, its expression appears to be restricted to the central nervous system (CNS). The 5-HT$_{2C}$ receptor subtype has been implicated in a wide variety of serotonin-mediated conditions including obesity, anxiety, depression, obsessive compulsive disorder, schizophrenia and migraine. In view of the different distributions of both receptor subtypes in human tissue, subtype selective compounds are expected to provide treatment of such serotonin-mediated disorders with a low likelihood of side-effects.

Recently, novel 5-HT$_{2C}$ selective compounds such as WAY-163909 (Dunlop J, *CNS Drug Reviews* 2006, 12(3), 167-177), CP-809,101 (Siuciak J. A, *Neuropharmacology* 2007, 52, 279-290) and (R)-9-ethyl-1,3,4,10b-tetrahydro-7-trifluoromethylpyrazino[2,1-a]isoindol-6(2H)-one (Wacker D. A et al, *J. Med. Chem.* 2007, 50(6), 1365-1379) have been reported to have robust dose-dependent positive effects on animal models of obesity, schizophrenia and cognitive dysfunction. In spite of the availability of these compounds, however, there remains a need for further 5-HT$_{2c}$ receptor modulators which are safe and effective.

WO 2007081299 relates to tricyclic indenopyrrole derivatives and to their use in the treatment of diseases, disorders and conditions wherein modulation of the activity of serotonin receptors is desired. U.S. Pat. No. 5,244,888, U.S. Pat. No. 5,049,564 and WO 199006927 relate to certain alkoxy substituted indenopyrrole, indenopyridine and benzisoindole derivatives indicated to be subtype selective compounds for 5-HT$_{1A}$ receptors and useful in the treatment of anxiety, depression and hypertension. U.S. Pat. No. 4,622,405 also relates to substituted indenopyrrole derivatives indicated to be useful in the treatment of hypertension. U.S. Pat. No. 4,618,683 relates to isoindoline derivatives indicated to be useful in the treatment of hypertension and as sedatives. EP 461353 relates to tetrahydrobenzisoindoline and octahydrobenzisoquinoline derivatives indicated to be biogenic amine uptake inhibitors and useful for the treatment of affective disorders, such as depression. EP 0222703 relates to hexahydrobenzopyranopyridine and hexahydrobenzothiopyranopyridine derivatives indicated to be 5-HT$_2$ receptor antagonists and useful for the treatment of psychotrophic disorders such as anxiety, depression and mania. Dihydroxy- and dimethoxy-octahydrobenzisoquinolines are described in *J. Med. Chem.* 1980, 23(5), 502-5. Quantitative structure-activity relationships for substituted aminotetralin analogs for both inhibition of norepinephrine and dopamine uptake have been described in *Journal of Pharmaceutical Sciences* 1993, 82(4), 355-61 and 521-5. Synthesis of octahydrobenzisoquinolines is described in *Tetrahedron Letters*, 1974, 1001.

In a first aspect, the present invention relates to a tricyclic heterocyclic derivative according to Formula I

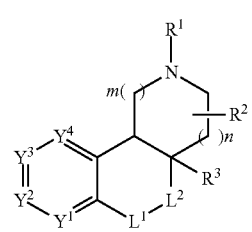

Formula I wherein
m is 1 or 2;
n is 0 or 1;
R$^1$ is H, C$_{1-6}$alkyl, C$_{2-6}$alkenyl, C$_{2-6}$alkynyl, C$_{3-7}$cycloalkyl, C$_{3-7}$cycloalkylC$_{1-2}$alkyl, C$_{1-2}$alkyloxyC$_{1-2}$alkyl or C$_{6-10}$arylC$_{1-2}$alkyl, said C$_{1-6}$alkyl, C$_{2-6}$alkenyl, C$_{2-6}$alkynyl, C$_{3-7}$cycloalkyl, C$_{3-7}$cycloalkylC$_{1-2}$alkyl, C$_{1-2}$alkyloxyC$_{1-2}$alkyl and C$_{6-10}$arylC$_{1-2}$alkyl each being optionally substituted with one or more halogens;
R$^2$ is H, C$_{1-4}$alkyl, C$_{3-5}$cycloalkyl or C$_{3-5}$cycloalkylC$_{1-2}$alkyl said C$_{1-4}$alkyl, C$_{3-5}$cycloalkyl and C$_{3-5}$cycloalkylC$_{1-2}$alkyl each being optionally substituted with one or more halogens;
R$^3$ is C$_{1-4}$alkyl, hydroxyC$_{1-2}$alkyl or C$_{1-2}$alkyloxyC$_{1-2}$alkyl said C$_{1-4}$alkyl and C$_{1-2}$alkyloxyC$_{1-2}$alkyl each being optionally substituted with one or more halogens;
L$^1$ is C=O, CR$^4$R$^5$;
L$^2$ is CR$^4$R$^{5'}$
R$^4$, R$^{4'}$, R$^5$ and R$^{5'}$ are each independently H, F, C$_{1-4}$alkyl, C$_{2-4}$alkenyl, C$_{2-4}$alkynyl, hydroxy, C$_{1-4}$alkyloxy, C$_{1-2}$alkyloxyC$_{1-2}$alkyl, C$_{3-5}$cycloalkyl or C$_{3-5}$cycloalkylC$_{1-2}$alkyl said C$_{1-4}$alkyl, C$_{3-5}$cycloalkyl and C$_{3-5}$cycloalkylC$_{1-2}$alkyl each being optionally substituted with one or more halogens or
one of R$^4$ and R$^{4'}$ together with one of R$^5$ and R$^{5'}$ along with the atoms to which they are bonded form a 3-6 membered ring optionally comprising a heteroatom selected from O, S and NR$^{4''}$, wherein R$^{4''}$ is H, C$_{1-4}$alkyl, COC$_{1-4}$alkyl or SO$_2$C$_{1-4}$alkyl.
Y$^1$ is N or CR$^6$;
Y$^2$ is N or CR$^7$;
Y$^3$ is N or CR$^8$;
Y$^4$ is N or CR$^9$ with the proviso that no more than two of Y$^1$-Y$^4$ can be N simultaneously;
R$^6$, R$^7$ and R$^8$ are each independently selected from H, C$_{1-6}$alkyl, C$_{2-6}$alkenyl, C$_{2-6}$alkynyl, C$_{3-7}$cycloalkyl, C$_{3-7}$cycloalkylC$_{1-2}$alkyl, C$_{1-6}$alkyloxy, SC$_{1-6}$alkyl, SOC$_{1-6}$alkyl, SO$_2$C$_{1-6}$alkyl, NR$^{10}$R$^{11}$, CO$_2$R$^{12}$, C$_{6-10}$aryl, C$_{1-10}$arylC$_{1-2}$alkyloxy, CN, halogen and a 5-6 membered heteroaryl ring system comprising 1-2 heteroatoms independently selected from N, O and S, wherein said C$_{1-6}$alkyl, C$_{3-7}$cycloalkyl, C$_{3-7}$cycloalkylC$_{1-2}$alkyl and C$_{1-6}$alkyloxy are each optionally substituted with one or more halogens and wherein said C$_{6-10}$aryl, 5-6 membered heteroaryl ring system comprising 1-2 heteroatoms independently selected from N, O and S and $C_{6-10}$aryl$C_{1-2}$alkyloxy are optionally independently substituted with one or more substitutents independently selected from methyl and halogen or;

$R^6$ and $R^7$ or $R^7$ and $R^8$ together with the atoms to which they are bonded form a 5-7 membered unsaturated ring optionally comprising 1-2 heteroatoms selected from $NR^{6'}$, O and S and optionally substituted with methyl or halogen, wherein $R^{6'}$ is H or $C_{1-4}$alkyl;

$R^9$ is H, $C_{1-6}$alkyl, $C_{3-7}$cycloalkyl, $C_{1-6}$alkyloxy, CN or halogen said $C_{1-6}$alkyl, $C_{3-7}$cycloalkyl and $C_{1-6}$alkyloxy each being optionally substituted with one or more halogens with the proviso that $R^6$-$R^9$ cannot simultaneously be H;

$R^{10}$ and $R^{11}$ are each independently H or $C_{1-6}$alkyl and $R^{12}$ is $C_{1-6}$alkyl;

or a pharmaceutically acceptable salt or solvate thereof.

The term $C_{1-6}$alkyl, as used herein, represents a branched or unbranched alkyl group having 1-6 carbon atoms. Examples of such groups are methyl, ethyl, isopropyl, tertiary butyl and n-pentyl. Similarly, the term $C_{1-4}$alkyl, as used herein, represents a branched or unbranched alkyl group having 1-4 carbon atoms. Examples of such groups are methyl, ethyl and isopropyl.

Likewise, the term $COC_{1-4}$alkyl, as used herein, represents a branched or unbranched carboxyalkyl group having 1-4 carbon atoms. Examples of such groups are carboxymethyl (i.e., acetyl), carboxyethyl and carboxyisopropyl.

The term $C_{2-6}$alkenyl, as used herein, represents a branched or unbranched alkenyl group having 2-6 carbon atoms and at least one double bond. Examples of such groups are ethenyl and isopropenyl. Similarly, the term $C_{2-4}$alkenyl, as used herein, represents a branched or unbranched alkenyl group having 2-4 carbon atoms. Examples of such groups are ethenyl and isopropenyl.

The term $C_{2-6}$alkynyl, as used herein, represents a branched or unbranched alkynyl group having 2-6 carbon atoms and at least one triple bond. Examples of such groups are ethynyl and pentynyl. Similarly, the term $C_{2-4}$alkynyl, as used herein, represents a branched or unbranched alkynyl group having 2-4 carbon atoms. Examples of such groups are ethynyl and propynyl.

The term $C_{3-7}$cycloalkyl, as used herein, represents a branched or unbranched cyclic alkyl group having 3-7 carbon atoms. Examples of such groups are cyclopropyl, cyclopentyl and 2-methylcyclohexyl. Similarly, the term $C_{3-5}$cycloalkyl, as used herein, represents a branched or unbranched cyclic alkyl group having 3-5 carbon atoms. Examples of such groups are cyclopropyl and 2-methylcyclobutyl.

The term $C_{3-7}$cycloalkyl$C_{1-2}$alkyl, as used herein, represents a $C_{1-2}$alkyl group which is substituted with a $C_{3-7}$cycloalkyl group. Examples of such groups are cyclopropylmethyl, and 2-cyclobutylethyl. Similarly, the term $C_{3-5}$cycloalkyl$C_{1-2}$alkyl, as used herein, represents a $C_{1-2}$alkyl group which is substituted with a $C_{3-5}$cycloalkyl group. Examples of such groups are cyclopropylmethyl and 2-methylcyclopropylmethyl.

The term $C_{1-6}$alkyloxy, as used herein, represents a branched or unbranched alkyloxy group having 1-6 carbon atoms. Examples of such groups are methoxy, ethoxy, isopropyloxy and tertiary butyloxy. Likewise the term $C_{1-4}$alkyloxy, as used herein, represents a branched or unbranched alkyloxy group having 1-4 carbon atoms.

The term $C_{1-4}$alkyloxy$C_{1-2}$alkyl, as used herein, represents a $C_{1-2}$alkyl group which is substituted with a $C_{1-4}$alkyloxy group. Examples of such groups are ethoxymethyl and methoxyethyl. Similarly, the term $C_{1-2}$alkyloxy$C_{1-2}$alkyl, as used herein, represents a $C_{1-2}$alkyl group which is substituted with a $C_{1-2}$alkyloxy group. Examples of such groups are ethoxymethyl and methoxyethyl.

The term $C_{6-10}$aryl, as used herein, represents an aromatic group having 6-10 carbon atoms and comprising one ring or two rings fused together, at least one of which must be aromatic. Examples of such groups include phenyl and naphthyl.

The term $C_{6-10}$aryl$C_{1-2}$alkyl, as used herein, represents a $C_{1-2}$alkyl group which is substituted with a $C_{6-10}$aryl group. Examples of such groups are benzyl and phenylethyl.

The term $C_{6-10}$aryl$C_{1-2}$alkyloxy, as used herein, represents a $C_{1-2}$alkyloxy group which is substituted with a $C_{6-10}$aryl group. Examples of such groups are benzyloxy and phenylethyloxy.

The term $SC_{1-6}$alkyl, as used herein represents a thioalkyl group having 1-6 carbon atoms, for example a $SCH_3$ or $SCH_2CH_3$ group. Similarly the term $SOC_{1-6}$alkyl, as used herein represents an alkylsulphinyl group having 1-6 carbon atoms, for example a $SOCH_3$ or $SOCH_2CH_3$ group and the term $SO_2C_{4-6}$alkyl, as used herein represents an alkylsulphonyl group having 1-6 carbon atoms, for example a $SO_2CH_3$ or $SO_2CH_2CH_3$ group.

The term halogen, as used herein, represents a fluorine, chlorine, bromine or iodine.

The term solvate, as used herein, refers to a complex of variable stoichiometry formed by a solvent and a solute (in this invention, a compound of Formula I). Such solvents may not interfere with the biological activity of the solute. Examples of suitable solvents include, water, ethanol and acetic acid.

Examples of 5 to 6 membered saturated or unsaturated heterocyclic ring systems comprising 1-2 heteroatoms selected from O, S and N include furan, pyrrole, thiophene, imidazole, pyrazole, thiazole, pyridine, pyrimidine, piperidine, pyrrolidine and tetrahydropyridine.

In one embodiment of the present invention, m is 1. In another embodiment, m is 2.

In a further embodiment of the present invention, n is 0. In another embodiment, n is 1.

In a further embodiment of the present invention, $R^1$ is H or $C_{1-6}$alkyl optionally substituted with one or more halogens. In another embodiment, $R^1$ is H or methyl. In another embodiment, $R^1$ is H.

In a further embodiment of the present invention, $R^1$ is $C_{3-7}$cycloalkyl$C_{1-2}$alkyl optionally substituted with one or more halogens. In another embodiment, $R^1$ is cyclopropylmethyl optionally substituted with one or more halogens.

In a further embodiment of the present invention, $R^1$ is $C_{6-10}$aryl$C_{1-2}$alkyl, optionally substituted with one or more halogens. In another embodiment, $R^1$ is benzyl optionally substituted with one or more halogens.

In a further embodiment of the present invention, $R^2$ is H or $C_{1-4}$alkyl optionally substituted with one or more halogens. In another embodiment, $R^2$ is H or methyl, optionally substituted with 1-3 halogens. In another embodiment, $R^2$ is H.

In a further embodiment of the present invention, $R^3$ is $C_{1-4}$alkyl optionally substituted with one or more halogens. In another embodiment, $R^3$ is methyl or ethyl optionally substituted with 1-3 halogens. In another embodiment, $R^3$ is hydroxymethyl. In another embodiment $R^3$ is methyl, ethyl, fluoromethyl, difluoromethyl or trifluoromethyl.

In a further embodiment of the present invention $R^4$, $R^{4'}$, $R^5$ and $R^{5'}$ are each independently H, F or $C_{1-4}$alkyl optionally substituted with one or more halogens. In another embodiment $R^4$, $R^{4'}$, $R^5$ and $R^{5'}$ are each independently H, F, methyl or ethyl, said methyl and ethyl being optionally substituted with 1-3 halogens. In another embodiment $R^4$, $R^{4'}$, $R^5$ and $R^{5'}$ are each independently H, F or methyl, optionally substituted with 1-3 halogens. In another embodiment, $R^4$, $R^{4'}$, $R^5$ and $R^{5'}$ are H.

In a further embodiment of the present invention, $Y^1$ is $CR^6$, wherein $R^6$ has the previously defined meanings;

In a further embodiment of the present invention, $Y^2$ is $CR^7$, wherein $R^7$ has the previously defined meanings;

In a further embodiment of the present invention, $Y^3$ is $CR^8$, wherein $R^8$ has the previously defined meanings;

In a further embodiment of the present invention, $Y^4$ is $CR^9$, wherein $R^9$ has the previously defined meanings;

In a further embodiment of the present invention, $R^6$ is H, $C_{1-6}$alkyl, $C_{2-6}$alkenyl, $C_{3-7}$cycloalkyl, $C_{1-6}$alkyloxy or halogen, said $C_{1-6}$alkyl, $C_{2-6}$alkenyl and $C_{1-6}$alkyloxy being optionally substituted with one or more halogens. In another embodiment, $R^6$ is H, methyl, difluoromethyl, trifluoromethyl, ethyl, ethylene, propyl, cyclopropyl, 2-methylpropyl, methoxy, bromo or chloro. In another embodiment, $R^6$ is H, F, difluoromethyl, trifluoromethyl, chloro, bromo, cyclopropyl or 2-methylpropyl.

In a further embodiment of the present invention, $R^6$ is a 5-6 membered saturated or unsaturated heterocyclic ring system comprising 1-2 heteroatoms independently selected from N, O and S.

In a further embodiment of the present invention, $R^7$ is H, $C_{1-6}$alkyl, $C_{3-7}$cycloalkyl, $C_{1-6}$alkyloxy, $C_{6-10}$aryl$C_{1-2}$alkyloxy or halogen, said $C_{1-6}$alkyl, $C_{1-6}$alkyloxy and $C_{6-10}$aryl$C_{1-2}$alkyloxy being optionally substituted with one or more halogens. In another embodiment, $R^7$ is H, methyl, trifluoromethyl, ethyl, propyl, cyclopropyl, 2-methylpropyl, methoxy, bromo or chloro.

In a further embodiment of the present invention, $R^8$ is H, $C_{1-6}$alkyl, $C_{3-7}$cycloalkyl, $C_{1-6}$alkyloxy, $C_{6-10}$aryl$C_{1-2}$alkyloxy or halogen, said $C_{1-6}$alkyl, $C_{1-6}$alkyloxy and $C_{6-10}$aryl$C_{1-2}$alkyloxy being optionally substituted with one or more halogens. In another embodiment, $R^8$ is H, methyl, ethyl, trifluoromethyl, OMe or cyclopropyl.

In a further embodiment of the present invention, $R^9$ is H, $C_{1-6}$alkyl, $C_{1-6}$alkyloxy or halogen, said $C_{1-6}$alkyl and $C_{1-6}$alkyloxy being optionally substituted with one or more halogens. In another embodiment, $R^9$ is H, methyl, ethyl, methoxy, bromo or chloro.

In a further embodiment of the present invention is a tricyclic heterocyclic derivative having the Formula II

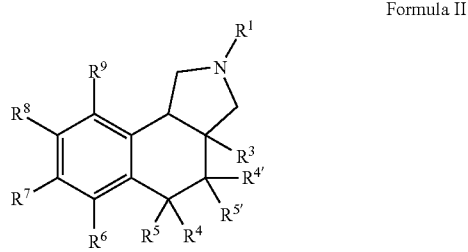

Formula II wherein $R^1$ and $R^3$-$R^9$ have the previously defined meanings or a pharmaceutically acceptable salt or solvate thereof.

In a further embodiment of the present invention is a tricyclic heterocyclic derivative having the Formula II, wherein
$R^1$ is H or methyl;
$R^3$ is methyl, ethyl, fluoromethyl, hydroxymethyl, difluoromethyl or trifluoromethyl;
$R^4$, $R^{4'}$, $R^5$, and $R^{5'}$ are independently H, F, methyl or ethyl;
$R^6$ is H, methyl, difluoromethyl, trifluoromethyl, chloro, bromo, cyclopropyl and 2-methylpropyl;
$R^7$ is H, methyl, trifluoromethyl, ethyl, propyl, cyclopropyl, 2-methylpropyl, methoxy, bromo or chloro;
$R^8$ is H, methyl, ethyl, trifluoromethyl or cyclopropyl and
$R^9$ is H, methyl, ethyl, methoxy, bromo or chloro with the proviso that $R^6$-$R^9$ cannot simultaneously be H
or a pharmaceutically acceptable salt or solvate thereof.

In a further embodiment of the present invention is a tricyclic heterocyclic derivative having the Formula III

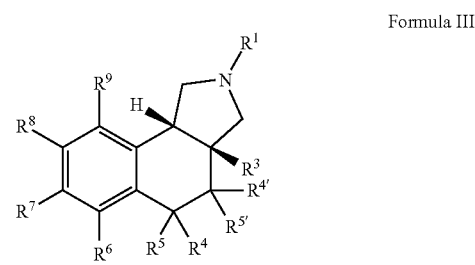

Formula III wherein $R^1$ and $R^3$-$R^9$ have the previously defined meanings or a pharmaceutically acceptable salt or solvate thereof.

In a further embodiment of the present invention is a tricyclic heterocyclic derivative having the Formula IV

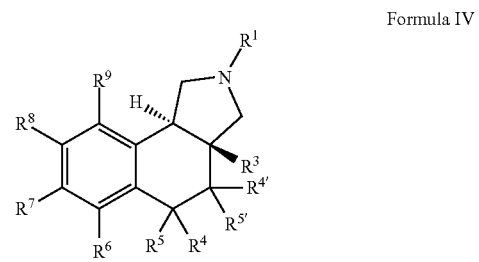

Formula IV wherein $R^1$ and $R^3$-$R^9$ have the previously defined meanings or a pharmaceutically acceptable salt or solvate thereof.

In a further embodiment is a tricyclic heterocyclic derivative selected from:

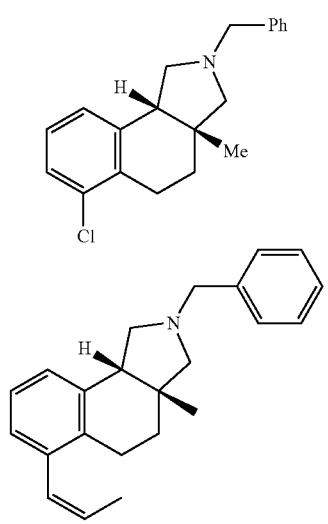

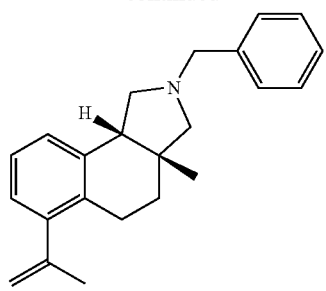
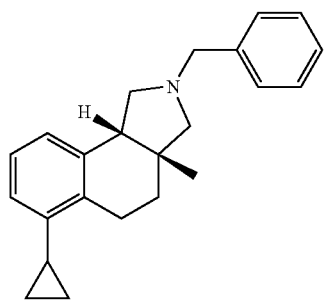
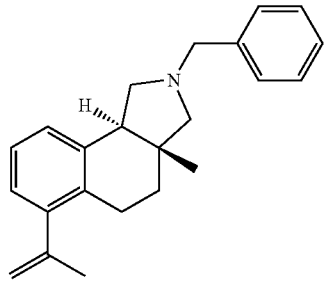
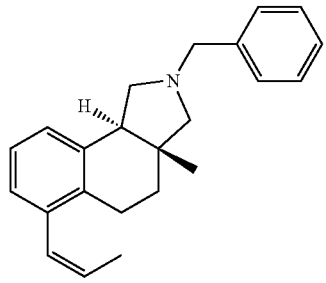
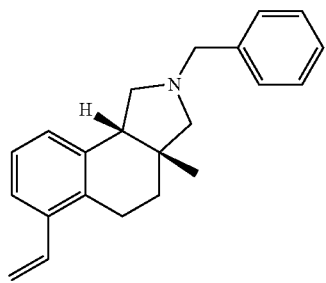
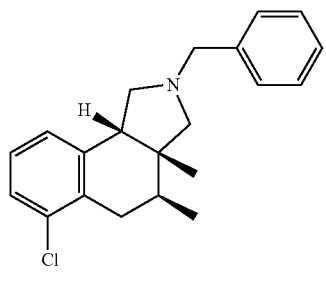
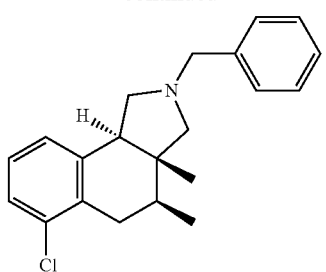
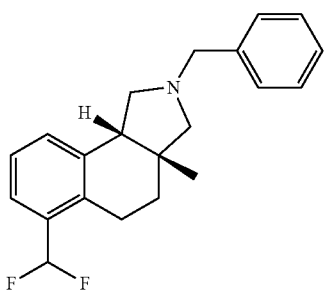
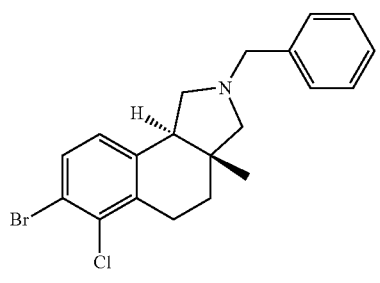
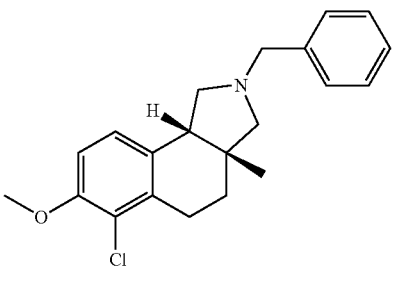
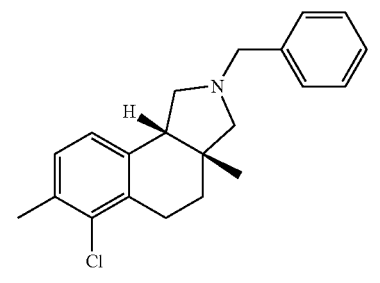
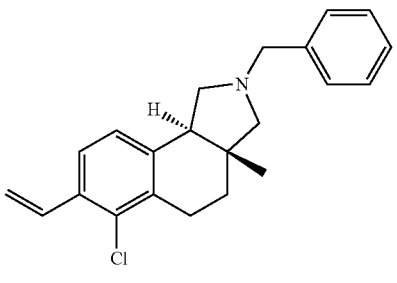

-continued
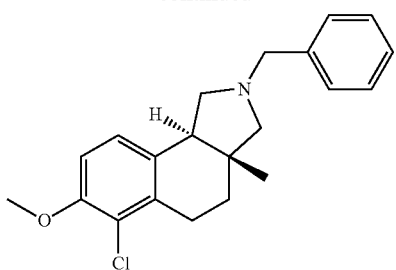
or a pharmaceutically acceptable salt or solvate thereof.
In a further embodiment is a tricyclic heterocyclic derivative selected from:
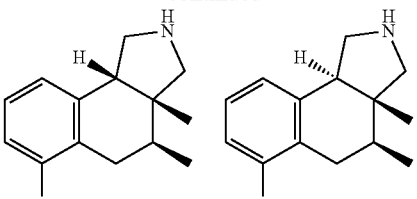
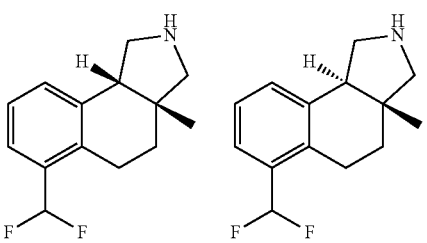
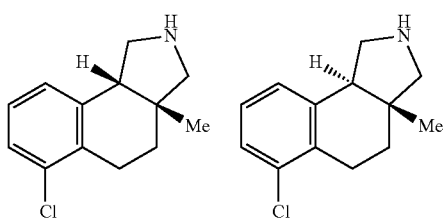
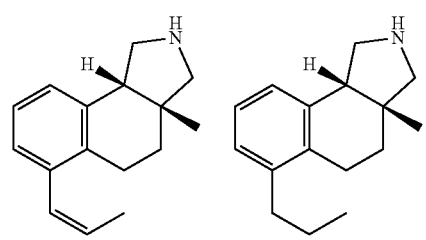
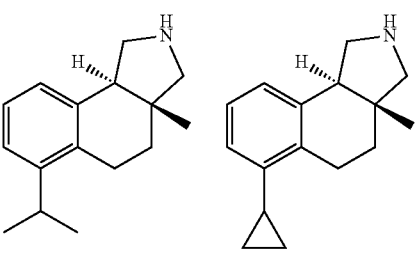
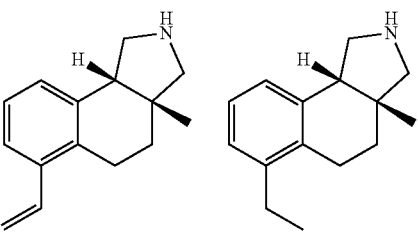
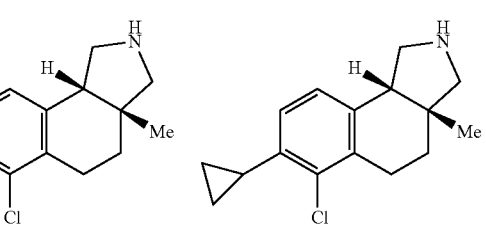
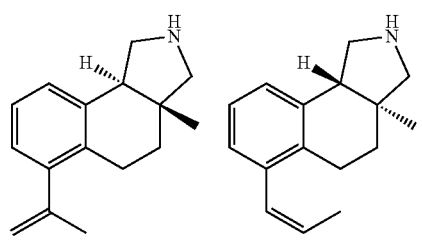
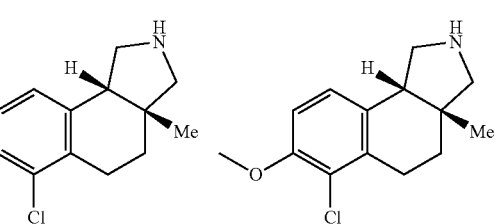
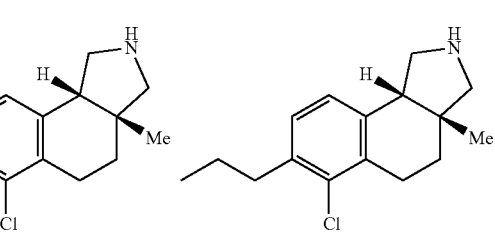

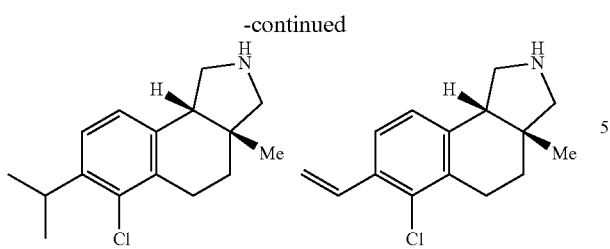
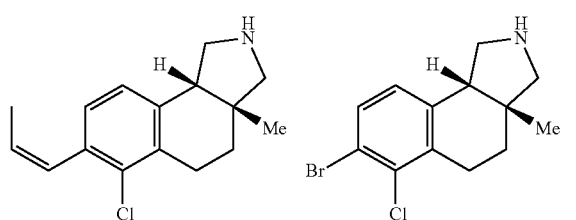
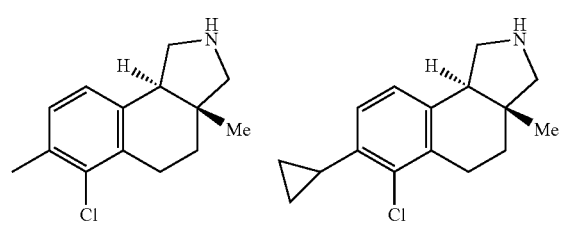
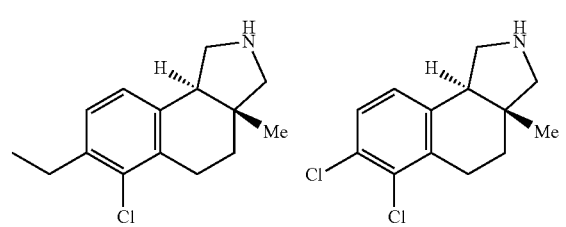
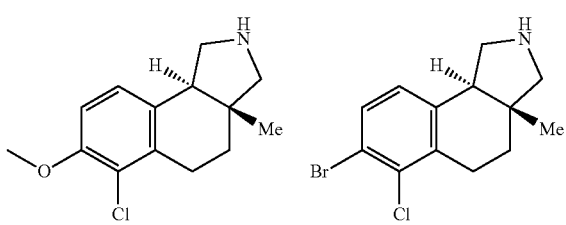
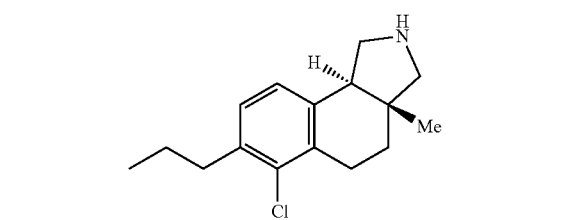
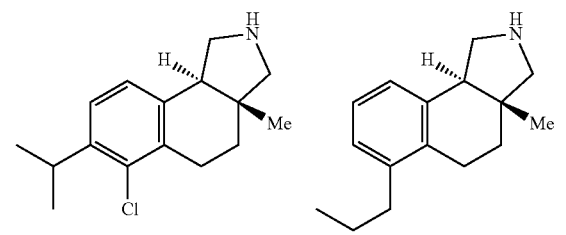

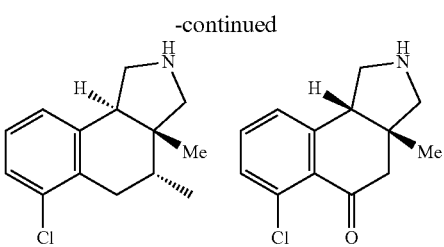
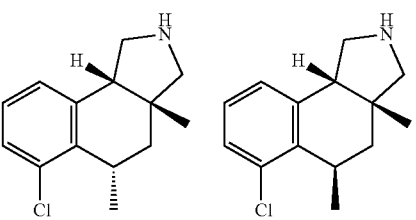

or a pharmaceutically acceptable salt or solvate thereof.

The tricyclic heterocyclic derivatives of the present invention are prepared by methods well known in the art of organic chemistry. See, for example, J. March, 'Advanced Organic Chemistry' 4$^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wuts 'Protective Groups in Organic Synthesis' 2$^{nd}$ Edition, John Wiley and Sons, 1991. The protective groups are optionally removed at a convenient subsequent stage using methods well known in the art. The various reagents and starting materials are either commercially available or are readily prepared using methods well known to the skilled person. The final products may then be further derivatised to provide other tricyclic heterocyclic derivatives according to the invention using conventional chemistry techniques. For example, further halogenation of aryl rings e.g., chlorination may be readily obtained using N-chlorosuccinimide in a suitable solvent, for example, methylene chloride.

The tricyclic heterocyclic derivatives of Formula I, wherein $L^1$-$L^2$ is $CR^4R^5$—$CR^{4'}R^{5'}$ e.g., hexahydrobenzisoindoles and octahydrobenzisoquinolines may be prepared, as shown in Scheme 1, from the appropriately substituted nitrile (1) itself prepared by well known methods (as shown in Scheme 2). Treatment of (1) with, for example, potassium hydroxide in ethanol and water, to affect hydrolysis of the nitrile affords the acid (2). Coupling of acid (2) with a suitable protected amino alkene (3) in the presence of a suitable coupling reagent and solvent, for example cyclophos or 1-hydroxybezotriazole hydrate and N,N'-methanediylidenedipropan-2-amine affords amide (4). Thermolysis of the benzocyclobutene alkene (4), for example by heating in 1,2-dichlorobenzene or bromobenzene provides a mixture of the cis- and trans-intramolecular Diels-Alder products (5) and (6), which are subsequently reduced using a suitable reducing agent, for example: LiAlH$_4$ or BH$_3$ DMS complex to yield the desired products (7) and (8). The amine of Formula (7) or (8), wherein $R^1$=H, can be prepared by deprotection of the amine (7) or (8), for example, wherein $R^1$ is benzyl the protecting group can be removed by hydrogenation with palladium on carbon or by heating with 1-chloroethyl chloroformate and quenching with methanol.

Scheme 1

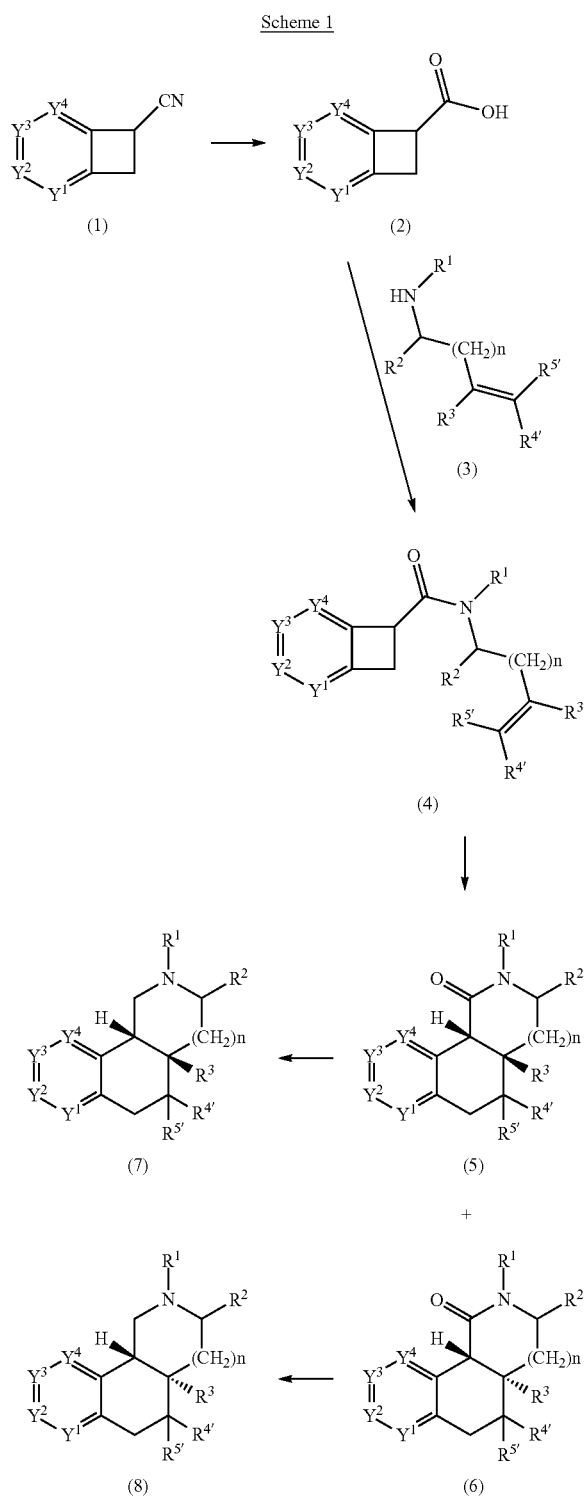

Scheme 2

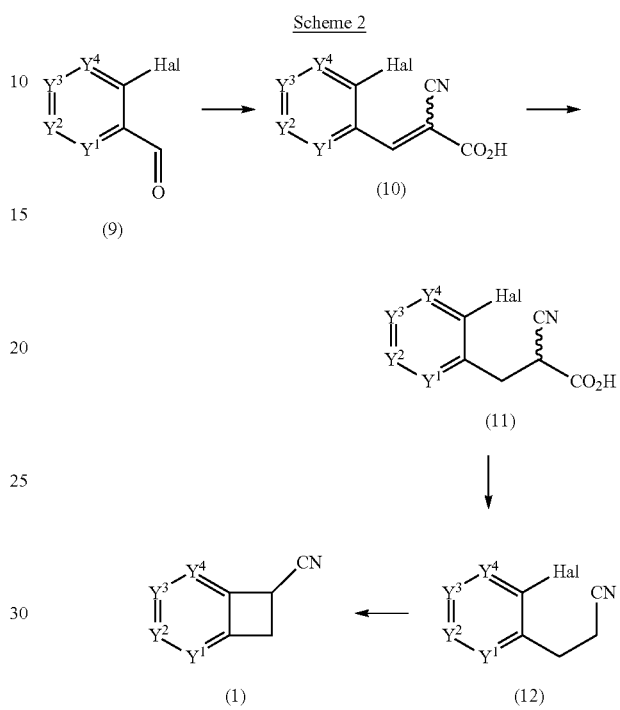

The cyclobutylnitrile (1), may be prepared as shown in Scheme 2, from the appropriately substituted o-halobenzaldehyde (9) (preferably wherein Hal=Br or Cl). For example, treatment of the o-halobenzaldehyde (9) with the appropriate cyanoacetic acid, pyridine and ammonium acetate in toluene provides the corresponding cinnamonitrile (10), which is subsequently reduced (sodium borohydride in ethanol) to give the dihydrocinnamonitrile (11). Decarboxylation by heating in the appropriate solvent (for example dimethyl acetamide) provides the nitrile (12), which upon subsequent ring closure using a suitable base, for example, sodium amide in ammonia affords the cyclobutylnitrile (1).

The hexahydrobenzindoles may be alternatively prepared from the appropriately substituted nitrile (1) by a sequence analogous to that of Scheme 1, but with the ring formation steps carried out in a different order (Scheme 3)—see Kametani, T. et al, *Journal of the Chemical Society, Perkin Transactions 1: Organic and Bio-Organic Chemistry* 1975, 19, 2001-4. Thermolysis of the benzocyclobutylnitrile (1) in the presence of the α,β-unsaturated ester (13), for example by heating in 1,2-dichlorobenzene or bromobenzene provides a mixture of the cis- and trans-Diels-Alder products (14). The nitrile (14) can then be reduced using, for example, $NiCl_2$ and $NaBH_4$ in ethanol to afford the amine (15) which can then be cyclised using a suitable base (for example triethylamine) and heating in a suitable solvent, for example toluene, to afford the cis- or trans-lactam (16). Reduction of the lactam (16) using a suitable reducing agent, for example: $LiAlH_4$ or $BH_3$ DMS complex affords the desired amine product (17).

Scheme 3

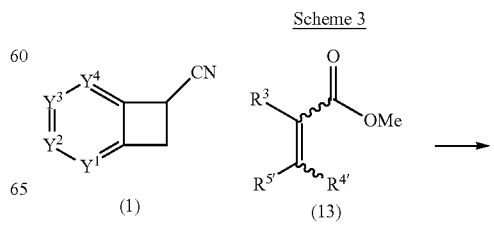

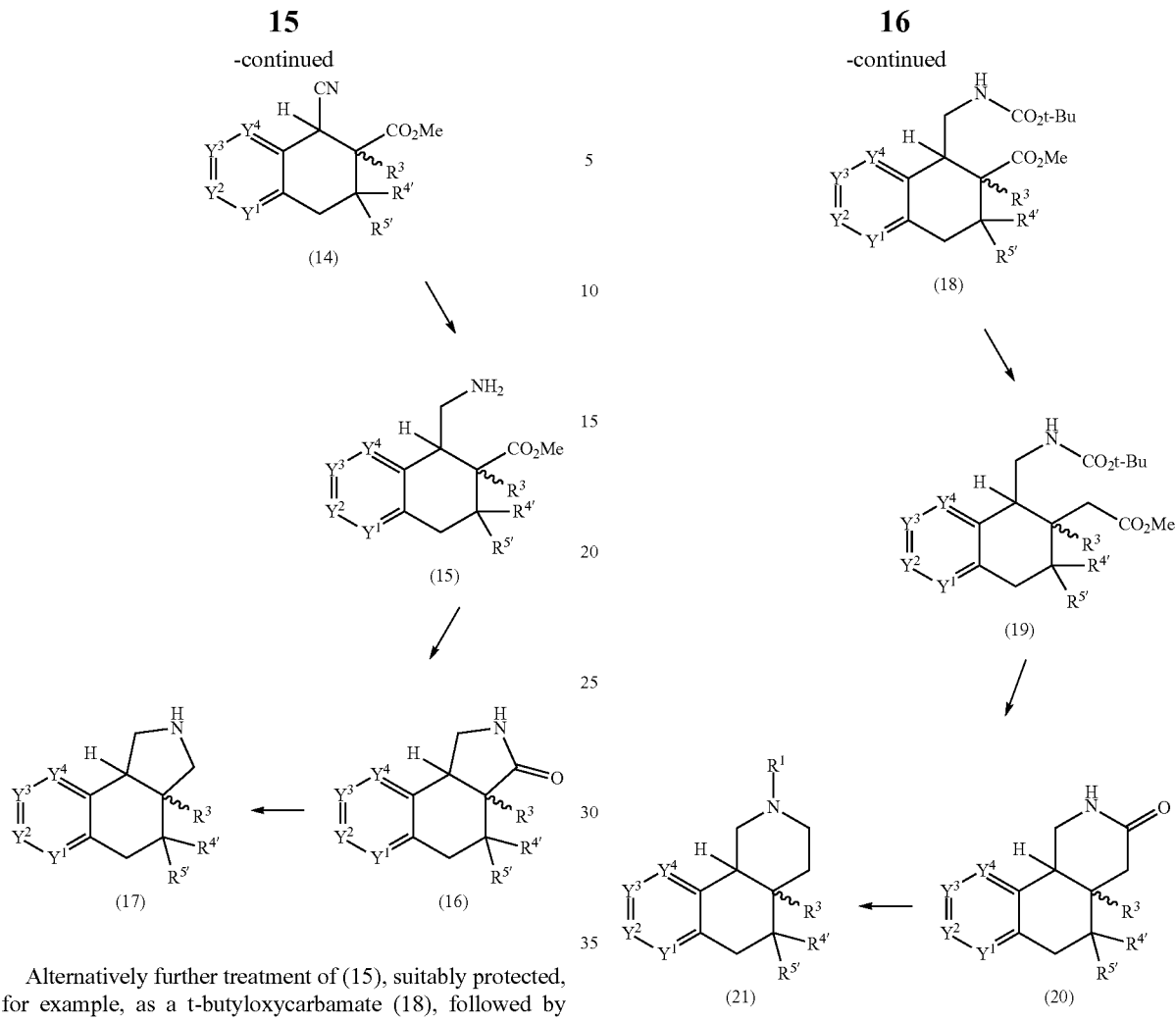

Alternatively further treatment of (15), suitably protected, for example, as a t-butyloxycarbamate (18), followed by homologation of the ester group results in the homologated ester (19). Homologation can be achieved by, for example, hydrolysis of (15) to the corresponding acid using aqueous sodium hydroxide in ethanol, followed by conversion to the acid chloride using thionyl chloride and subsequent treatment with diazomethane to generate the alpha-diazoketone for subsequent Arndt-Eistert homologation using Ag(OBz)$_2$ and methanol to afford the ester (19). Deprotection using trifluoroacetic acid followed by intramolecular ring closure using a suitable base, for example, sodium methoxide in ethanol affords the lactam (20) which can be subsequently reduced to the desired amine product (21) using, for example LiAlH$_4$ or BH$_3$ DMS complex and functionalised to form further R$^1$ as desired, for example by appropriate reductive alkylation of the required aldehyde in the presence of sodium triacetoxyborohydride in ethanol (Scheme 4).

Scheme 4

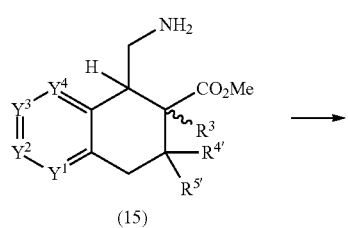

(15)

The tricyclic derivatives (26) may also be prepared as shown in Scheme 5, from the appropriately substituted acid (2). Coupling of acid (2) with a suitable amine NHR$^1$ (wherein, for example R$^1$=Bn) using, for example, 1-hydroxybezotriazole hydrate and N, N'-methanediylidenedipropan-2-amine affords the intermediate amide which may then be reduced, using for example lithium aluminium hydride in DMF, to afford the corresponding amine (22). The amine (22) can then be coupled with a suitable alkene substituted acid (23), again using 1-hydroxybezotriazole hydrate and N,N'-methanediylidenedipropan-2-amine to afford the corresponding amide (24). Thermolysis of the benzocyclobutylalkene (24), for example by heating in 1,2-dichlorobenzene, bromobenzene or 1,4-dioxane provides a mixture of the cis- and trans-intramolecular Diels-Alder products (25). The desired amine product (26) can be obtained by reduction of the amide (25) using a suitable reducing agent, for example: LiAlH$_4$ or BH$_3$ DMS complex, followed by deprotection of the benzyl group by hydrogenation with palladium on carbon or by heating with 1-chloroethyl chloroformate and quenching with methanol. Appropriate R$^1$ groups can be introduced by N-alkylation of the secondary amine with an appropriate alkylhalide, for example benzylbromide, or by reductive amination with an appropriate aldehyde, for example formaldehyde.

Scheme 5

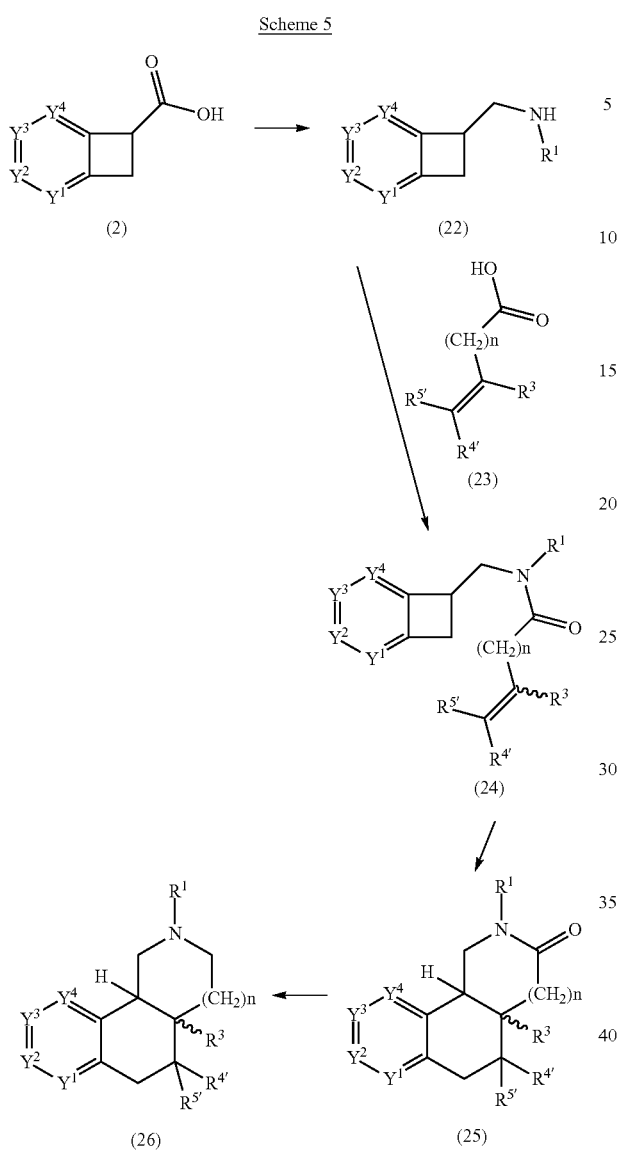

The octahydronaphthazepine (32) (i.e., compounds of Formula I, wherein $L^1=L^2=$ is $CH_2$, m is 2 and n is 1) may be prepared as shown in Scheme 6 from the appropriately substituted acid (2). Homologation of (2) can be achieved by, for example, hydrolysis of (2) to the corresponding acid using aqueous sodium hydroxide in ethanol, followed by conversion to the acid chloride using thionyl chloride and subsequent treatment with diazomethane to generate the alpha-diazoketone for subsequent Arndt-Eistert homologation using $Ag(OBz)_2$ and methanol to afford the ester (27). The ester (27) can then be readily converted to the amine (28) using standard techniques well known in the art of organic chemistry, for example, following hydrolysis of the ester group, amide coupling with a suitable amine $NHR^1$ (wherein, for example $R^1$=Bn) in the presence of a suitable coupling reagent, for example cyclophos or 1-hydroxybezotriazole hydrate and N, N'-methanediylidenedipropan-2-amine, followed by reduction, using for example lithium aluminium hydride in THF to afford the amine (28). The amine (28) may be coupled with a suitable alkene substituted acid (29) to afford the corresponding amide (30) again in the presence of, for example, cyclophos or 1-hydroxybezotriazole hydrate and N,N'-methanediylidenedipropan-2-amine. Thermolysis of the benzocyclobutene alkene (30), for example by heating in 1,2-dichlorobenzene, provides a mixture of the cis- and trans-intramolecular Diels-Alder products (31). The desired amine product (32) can be obtained by reduction of the amide (31) using a suitable reducing agent (for example: $LiAlH_4$ or $BH_3$ DMS complex) and then further functionalised to introduce the appropriate $R^1$, for example, by removal of the benzyl protecting group by hydrogenation with palladium on carbon or by heating with 1-chloroethyl chloroformate and quenching with methanol, followed by, for example, reductive amination with an appropriate aldehyde in the presence of, for example, sodium triacetoxyborohydride in ethanol.

Scheme 6

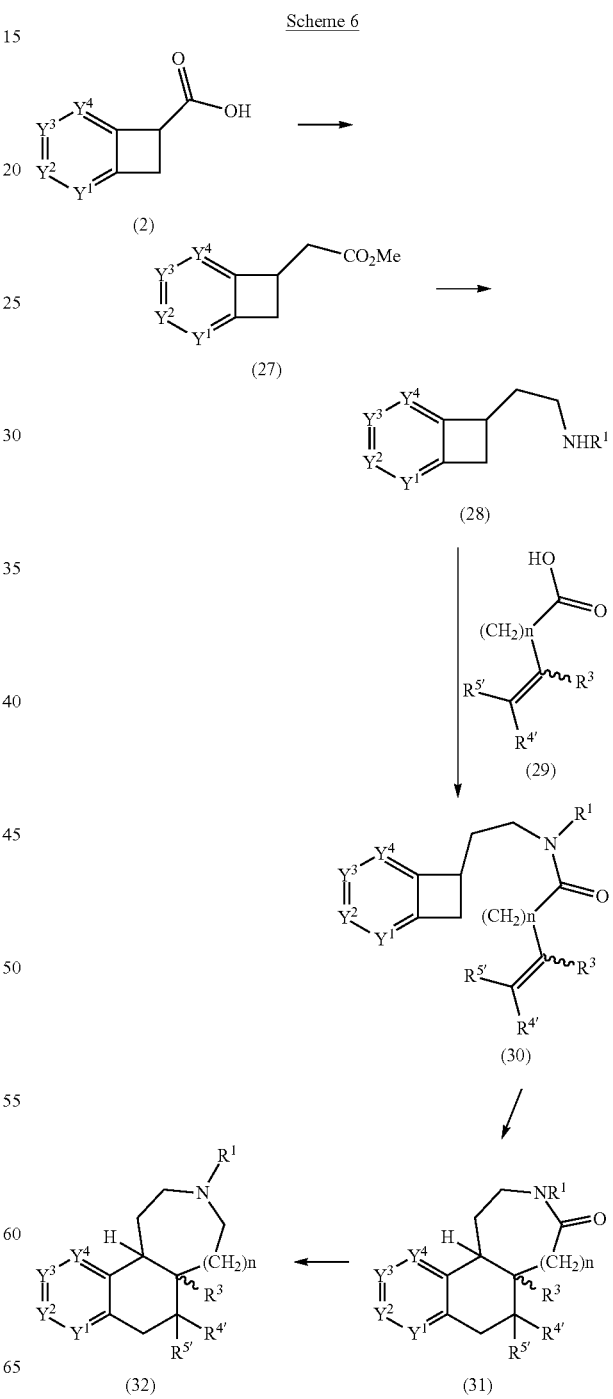

Hexahydroisoquinoline derivatives (39) and (40) (wherein $L^1$-$L^2$ is $CR^4R^5$—$CR^{4'}R^{5'}$) are prepared as outlined in Scheme 7. Treatment of the keto ester (33) with t-butyl-2-cyanoethanoate yields the unsaturated nitrile (34). This can then be reduced in the presence of, for example, sodium borohydride in ethanol to provide the nitrile (35). Alkylation of nitrile (35), for example using an alkyl halide and suitable base (for example NaH in DMF), can be used to obtain nitrile (36). Selective removal of the t-butyl group using for example, trifluoroacetic acid, followed by heating yields the nitrile (37). This can then be treated with, for example, sodium borohydride and nickel chloride in ethanol to obtain the lactam (38), which can then be subsequently converted to the piperidine (40) by reduction of the lactam using, for example $LiAlH_4$ or $BH_3$ DMS complex, followed by subsequent functionalisation to introduce the required $R^1$, for example using the appropriate $R^1$-halide in the presence of a suitable base and solvent.

Incorporation of $R^4$ and $R^5$ can be achieved by a benzylic oxidation (for example using cerium oxide and sodium bromate) of appropriately protected (Formula I), for example as the ethyl carbamate (i.e. $R^1$=$CO_2Et$) gives benzylic ketone (41). Methods well known in the art can then be used to add $R^4$ and $R^5$. For example, addition of an alkyl or aryl lithium (RLi) can be used to incorporate and alkyl or aryl group into the $R^4$/$R^5$ position. Similarly, reducing agents, such as $NaBH_4$, can be used to incorporate an H atom at the $R^4$/$R^5$ position. Alkylation of the free OH using, for example, sodium hydride and methyl iodide can then be used to incorporate, for example, a methyl ether at the $R^4$/$R^5$ position. Deprotection (where $R^1$ is an ethyl carbamate) can then be affected by heating in a methanolic solution of potassium hydroxide to afford product (42) where $R^1$=H. Alkylation can then be achieved by reductive amination with an appropriate aldehyde in the presence of, for example, sodium triacetoxyborohydride in ethanol (Scheme 8).

Other reactions well know in the art can also be used to incorporate substitution at the $R^4$/$R^5$ positions. These include, but are not exhausted by, the Wittig reaction, that can be used to introduce an alkene group at the $R^4$/$R^5$ position. Subsequent hydrogenation or further derivatisation may then be applied.

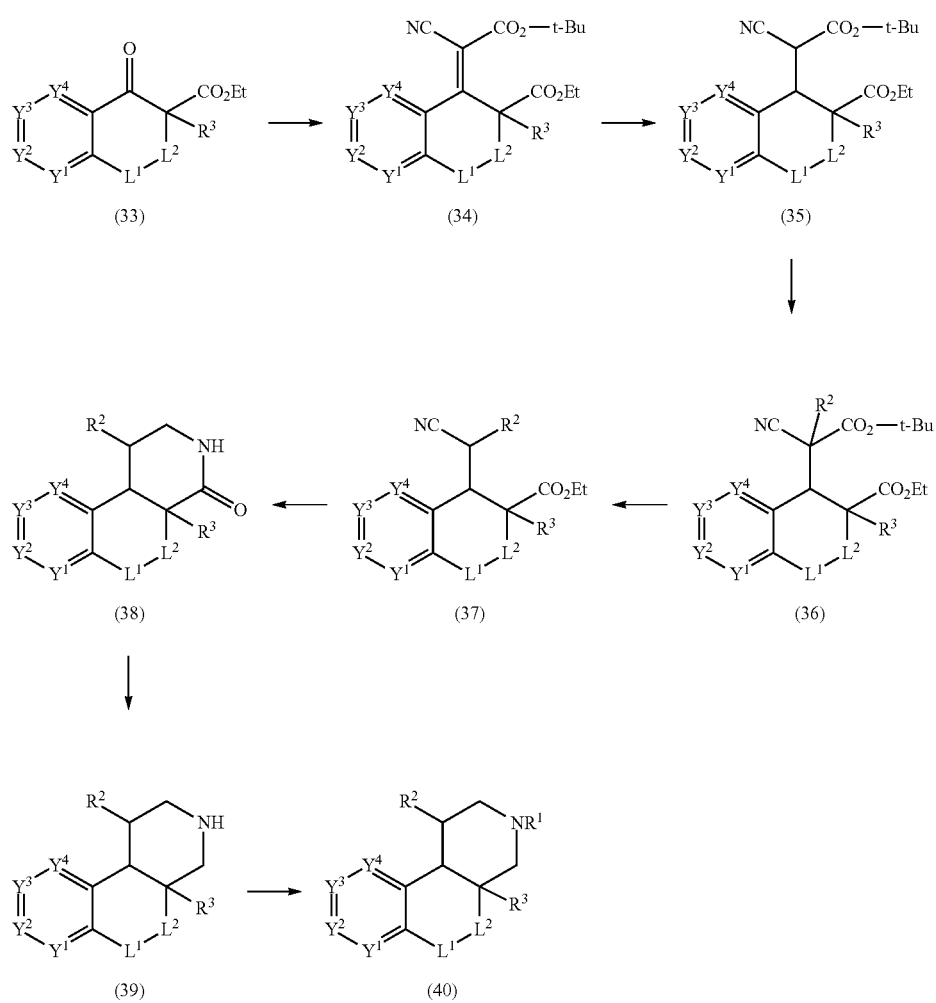

Scheme 7

Scheme 8

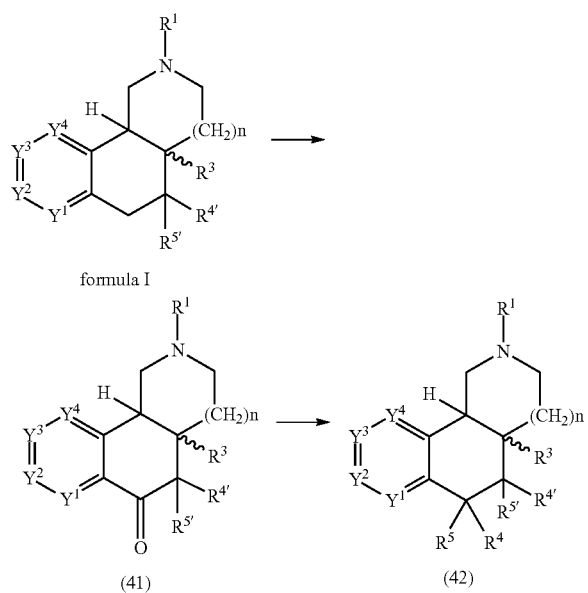

formula I (41)

(42)

The present invention also includes within its scope all stereoisomeric forms of the tricyclic heterocyclic derivatives according to the present invention resulting, for example, because of configurational or geometrical isomerism. Such stereoisomeric forms are enantiomers, diastereoisomers, cis and trans isomers etc. For example, in the case where $R^1$=H, the compound exists as a pair of enantiomers for each of the cis- and trans-geometrical isomers. In the case of the individual stereoisomers of heterocyclic derivatives of Formula I or salts or solvates thereof, the present invention includes the aforementioned stereoisomers substantially free, i.e., associated with less than 5%, preferably less than 2% and in particular less than 1% of the other stereoisomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g., synthesis with chiral induction, synthesis starting from chiral intermediates, enantioselective enzymatic conversions, separation of stereoisomers using chromatography on chiral media. Such methods are described in *Chirality In Industry* (edited by A. N. Collins, G. N. Sheldrake and J. Crosby, 1992; John Wiley and sons). Likewise methods for synthesis of geometrical isomers are also well known in the art.

The tricyclic heterocyclic derivatives of the present invention, in the form as a free base, are isolated from reaction mixtures as pharmaceutically acceptable salts. These salts are also obtained by treatment of said free base with an organic or inorganic acid, for example, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulfonic acid, fumaric acid, succinic acid, tartaric acid, citric acid, benzoic acid and ascorbic acid.

The tricyclic heterocyclic derivatives of the present invention also exist as amorphous forms. Multiple crystalline forms are also possible. All these physical forms are included within the scope of the present invention.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 51), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The present invention also embraces isotopically-labelled compounds of the tricyclic heterocyclic derivatives described and claimed herein which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine, chlorine and iodine such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$ respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically labeled compounds of formula (I) can be useful for medical imaging purposes, e.g., those labeled with positron-emitting isotopes, like $^{11}C$ or $^{18}F$ can be useful for application in Positron Emission Tomography (PET) and those labeled with gamma ray emitting isotopes, like $^{123}I$, can be useful for application in single photon emission computed tomography (SPECT). Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

Prodrugs of the tricyclic heterocyclic derivatives of the invention are also contemplated within the scope of the invention. A prodrug is a compound which acts as a drug precursor which, upon administration to a subject, undergoes conversion by metabolic or other chemical processes to yield a heterocyclic derivative of Formula I or a solvate or salt thereof. For example, where $R^3$ is $CH_2OH$, the hydroxyl group may be capped as, for example, an ester or a carbamate, which upon administration to a subject will undergo conversion back to the free hydroxyl group. A discussion of prodrugs is provided in T. Higuchi and V. Stella, *Pro-drugs as Novel Delivery Systems* 1987, 14 of the A.C.S. Symposium Series, and in *Bioreversible Carriers in Drug Design*, 1987, Edward B. Roche, ed., American Pharmaceutical Association and Pergamon Press. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In a further aspect, the tricyclic heterocyclic derivatives of the present invention and their pharmaceutically acceptable salts and solvates are useful in therapy. In particular, the tricyclic heterocyclic derivatives of the present invention are useful in therapy in humans or animals. As such the tricyclic heterocyclic derivatives of the present invention are useful for the manufacture of a medicament for the treatment or prevention of serotonin mediated disorders. In particular the tricyclic heterocyclic derivatives of the present invention are useful for the manufacture of a medicament for the treatment of obesity, diabetes (type I and type II), diabetic complications, atherosclerosis, impared glucose tolerance and dyslipidemia, anxiety, depression, obsessive compulsive disorder, panic disorder, psychosis, schizophrenia, sleep disorder, sexual disorder and social phobias; cephalic pain; migraine and gastrointestinal disorders. In a further aspect the present invention includes a tricyclic heterocyclic derivative for use in the treatment or prevention of any of the aforementioned diseases or disorders.

The present invention further includes a method for the treatment of a mammal, including a human, suffering from or liable to suffer from any of the aforementioned diseases or disorders, which comprises administering an effective amount of a tricyclic heterocyclic derivative according to the present invention or a pharmaceutically acceptable salt or solvate thereof. By effective amount or therapeutically effective amount is meant an amount of compound or a composition of the present invention effective in inhibiting the above-noted diseases and thus producing the desired therapeutic, ameliorative, inhibitory or preventative effect.

The amount of a tricyclic heterocyclic derivative of the present invention or a pharmaceutically acceptable salt or solvate thereof, also referred to herein as the active ingredient, which is required to achieve a therapeutic effect will, of course, vary with the particular compound, the route of administration, the age and condition of the recipient and the particular disorder or disease being treated.

A suitable daily dose for any of the above mentioned disorders will be in the range of 0.001 to 50 mg per kilogram body weight of the recipient (e.g. a human) per day, preferably in the range of 0.01 to 20 mg per kilogram body weight per day. The desired dose may be presented as multiple sub-doses administered at appropriate intervals throughout the day.

Whilst it is possible for the active ingredient to be administered alone, it is preferable to present it as a pharmaceutical composition. The present invention therefore also provides a pharmaceutical composition comprising a tricyclic heterocyclic derivative according to the present invention in admixture with one or more pharmaceutically acceptable excipients, such as the ones described in Gennaro et. al., Remmington: *The Science and Practice of Pharmacy*, 20$^{th}$ Edition, Lippincott, Williams and Wilkins, 2000; see especially part 5: pharmaceutical manufacturing. Suitable excipients are described e.g., in the Handbook of Pharmaceutical Excipients, 2$^{nd}$ Edition; Editors A. Wade and P. J. Weller, American Pharmaceutical Association, Washington, The Pharmaceutical Press, London, 1994. Compositions include those suitable for oral, nasal, topical (including buccal, sublingual and transdermal), parenteral (including subcutaneous, intravenous and intramuscular) or rectal administration.

The mixtures of a tricyclic heterocyclic derivative according to the present invention and one or more pharmaceutically acceptable excipient or excipients may be compressed into solid dosage units, such as tablets, or be processed into capsules or suppositories. By means of pharmaceutically suitable liquids the compounds can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The tricyclic heterocyclic derivatives of the invention are also suitable for use in an implant, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The present invention further includes a pharmaceutical composition, as hereinbefore described, in combination with packaging material suitable for said composition, said packaging material including instructions for the use of the composition for the use as hereinbefore described.

The invention is further illustrated by the following examples which are not intended to limit the scope thereof. Unless otherwise indicated, percent is percent by weight given the component and the total weight of the composition, temperature is in ° C. or is at ambient temperature and pressure is at or near atmospheric. Commercial reagents were used without further purification.

METHODS

General Chemical Procedures. All reagents were either purchased from common commercial sources or synthesised according to literature procedures using commercial sources. Commercial reagents were used without further purification.

All NMR spectra were recorded using a Bruker AC400 spectrometer. Chemical shifts were recorded in parts per million using TMS as a standard. Mass spectra were recorded on a Shimadzu LC-8A (HPLC) PE Sciex API 150EX LCMS. Analytical reversed-phase LCMS analysis was carried out on LUNA C18 column (5µ; 30×4.6 mm) under gradient conditions (90% water/0.1% formic acid to 90% acetonitrile/0.1% formic acid) at a flow rate of 4 mL/min.

For chromatography eluent: x-y % solvent A in solvent B means that a gradient of the eluent of x % (v/v) of solvent A in solvent B to y % (v/v) of solvent A in solvent B was used.

ABBREVIATIONS

Dimethylformamide (DMF), dimethylacetamide (DMA), 1,2-dimethoxyethane (DME), dichloromethane (DCM), dimethylsulphoxide (DMSO), tetrahydrofuran (THF), high pressure liquid chromatography (HPLC), diisopropylethylamine (DIPEA), triethylamine (TEA), trifluoroacetic acid (TFA), tert-butyloxycarbonyl (Boc), dimethylsulphide (DMS), diaza-1,5-bicyclo[4,3,0]non-5-ene (DBN), benzyl (Bn), sat (saturated), conc (concentrated), aq (aqueous), rt (room temperature), fcc (flash (silica) column chromatography), para-methoxybenzyl (PMB), lithiumdiisopropylamide (LDA), meta-chloroperbenzoic acid (m-CPBA), potassium hexamethyldisilylazide (KHMDS), tris(2-(2-methoxyethoxy)ethyl)amine (TDA-1) and 1-chloroethyl chloroformate (ACE-Cl), N-methyl pyrrolidinone (NMP).

EXAMPLE 1 cis-6-Chloro-3a-methyl-2,3,3a,4,5,9b-hexahydro-1H-benzo[e]isoindole

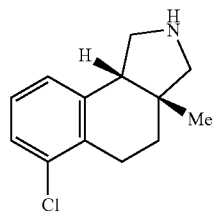 [SMILES: C[C@@]12CCc3c(Cl)cccc3[C@@H]1CNC2]

1.1 Preparation of 3-chloro-1,2-dihydrocyclobutabenzene-1-carboxylic acid

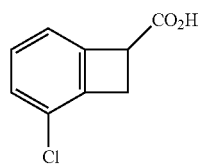 [SMILES: O=C(O)C1Cc2c(Cl)cccc21]

1.1.1 Preparation of 2-cyano-3-(2,6-dichlorophenyl)acrylic acid

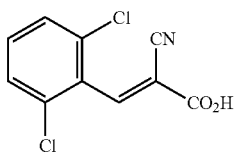 [SMILES: N#C/C(=C\c1c(Cl)cccc1Cl)C(=O)O]

A stirred mixture of 2,6-dichlorobenzaldehyde (609 mmol, 106.5 g), cyanoacetic acid (609 mmol, 51.8 g), ammonium acetate (122 mmol, 9.38 g), pyridine (1065 mmol, 86 ml, 84 g) and toluene (468 ml) was stirred at reflux using a Dean-Stark apparatus until one equivalent of water was collected (NB Oil bath temperature should not exceed 120° C. to avoid decarboxylation at this stage—lag Dean-Stark well). The reaction mixture was allowed to cool and the solid precipitate filtered and stirred with 10% aqueous HCl. The solid was again collected by filtering to afford pure 2-cyano-3-(2,6-dichlorophenyl)acrylic acid (7.21 g). The filtrate was concentrated in vacuo to give the crude 2-cyano-3-(2,6-dichlorophenyl)acrylic acid (~135 g). Recrystallisation from toluene afforded pure 2-cyano-3-(2,6-dichlorophenyl)acrylic acid (101 g).

1.1.2 Preparation of 2-cyano-3-(2,6-dichlorophenyl)propanoic acid

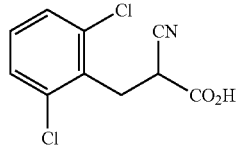

Sodium borohydride (1121 mmol, 42.4 g) was added, in portions over a period of 45 minutes, to a stirred suspension of 2-cyano-3-(2,6-dichlorophenyl)acrylic acid (448 mmol, 108.5 g) in MeOH (1 L) and aqueous saturated sodium bicarbonate (500 mL) at 0° C. After stirring at 0° C. for 30 minutes the cooling bath was removed and the reaction was allowed to warm to room temperature. Stirring was continued at room temperature for 3 hours and the reaction mixture was then left to stand overnight. The reaction mixture was partially concentrated under reduced pressure and the remaining aqueous was diluted with water and then acidified with 5 N HCl. Extraction with ether followed by drying over sodium sulfate, filtering and concentrating under reduced pressure afforded 110 g of 2-cyano-3-(2,6-dichlorophenyl)propanoic acid (100% yield).

1.1.3 Preparation of 3-(2,6-dichlorophenyl)propanenitrile

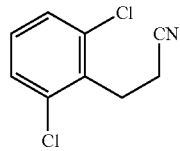 [SMILES: N#CCCc1c(Cl)cccc1Cl]

2-Cyano-3-(2,6-dichlorophenyl)propanoic acid (447 mmol, 109 g) was dissolved in DMA (179 ml) and heated for 2 hours at 150° C. After cooling, the reaction mixture was poured into water and extracted with ether. The organic layer was washed with a saturated solution of sodium hydrogen carbonate and then with a saturated solution of sodium chloride. The organic phase was dried over sodium sulfate and concentrated under reduced pressure to afford 3-(2,6-dichlorophenyl)propanenitrile (94% yield, 83.8 g).

1.1.4 Preparation of 3-chloro-1,2-dihydrocyclobutabenzene-1-carbonitrile

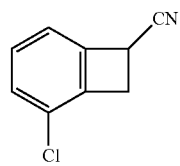 [SMILES: N#CC1Cc2c(Cl)cccc21]

A dried 2 L 3-neck flask was fitted with a card-ice condenser, sealed under nitrogen and cooled to −78° C. Ammonia gas was condensed into the flask from a cylinder until approximately required volume was present (~300 mL).

Commercial sodium amide (800 mmol, 31.2 g) was added to the ammonia at −78° C. and after stirring for 10 minutes 3-(2,6-dichlorophenyl)propanenitrile (200 mmol, 40 g) was added over a 5 minute period. The mixture was allowed to warm such that the resultant mixture was stirred at reflux for 4 h before being neutralised with solid ammonium nitrate (800 mmol, 64.0 g) and allowed to stand overnight under a flow of nitrogen. The ammonia was evaporated and water was added to the solid residue and the products were extracted with dichloromethane (×3). The combined organics were washed with dilute hydrochloric acid (5%), followed by water. The organics were dried with sodium sulfate and concentrated to afford crude 3-chloro-1,2-dihydrocyclobutabenzene-1-carbonitrile as a brown residue (98% yield, 32 g).

1.1.5 Preparation of 3-chloro-1,2-dihydrocyclobutabenzene-1-carboxylic acid

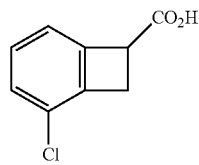 [SMILES: O=C(O)C1Cc2c(Cl)cccc21]

A solution of 3-chloro-1,2-dihydrocyclobutabenzene-1-carbonitrile (196 mmol, 32 g) and potassium hydroxide (978 mmol, 54.9 g) in EtOH (500 ml)/water (100 ml) was stirred at reflux for 2 h. After evaporation of the organic solvent, the aqueous residue was washed with Et$_2$O. The organic layer was extracted with 2N NaOH aq. and combined aqueous layers were acidified with 5 N HCl and extracted with Et$_2$O. The extracts were washed with brine, dried over Na$_2$SO$_4$ and concentrated in vacuo. The residue was washed with heptane/Et$_2$O (5/1) to afford 3-chloro-1,2-dihydrocyclobutabenzene-1-carboxylic acid (85% yield, 30.3 g).

1.2 Preparation of N-benzyl-2-methylprop-2-en-1-amine

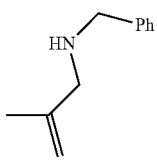

Benzylamine (16.17 ml, 148 mmol), 3-bromo-2-methylprop-1-ene (37.0 mmol, 3.73 ml, 5 g) and sodium bicarbonate (37.0 mmol, 3.11 g) were stirred in water (20 ml) at 95° C. for 4 h. The reaction mixture was acidified to pH 1 using aqueous HCl (5 N) and washed with EtOAc. The phases were separated and the aqueous was basified to pH 13/14 using NaOH (4 N) and extracted with EtOAc (2×50 ml). The combined organic extracts were dried over Na$_2$SO$_4$, filtered and concentrated in vacuo to give an orange/brown oil (16.78 g). 5 g of the crude product was then purified by silica column chromatography (5-10% MeOH in DCM) to afford N-benzyl-2-methylprop-2-en-1-amine (1.28 g) as a yellow oil. $^1$H NMR (400 MHz, CDCl$_3$) ppm 7.33-7.21 (5H, m, ArH), 4.90 (1H, s, alkenyl-H), 4.85 (1H, s, alkenyl-H), 3.77 (2H, s, benzylic-CH$_2$), 3.20 (2H, s, NHCH$_2$C(CH$_2$)CH$_3$), 1.77 (3H, s, CH$_3$).

1.3. Preparation of N-benzyl-3-chloro-N-(2-methylallyl)-1,2-dihydrocyclobutabenzene-1-carboxamide

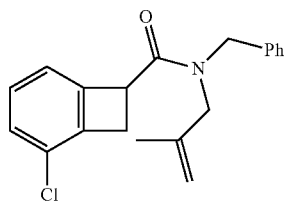 [SMILES: C=C(C)CN(Cc1ccccc1)C(=O)C1Cc2c(Cl)cccc21]

To a solution of 3-chloro-1,2-dihydrocyclobutabenzene-1-carboxylic acid (7.67 mmol, 1.4 g) in DCM (20 ml) was added N-benzyl-2-methylprop-2-en-1-amine (11.50 mmol, 1.854 g), triethylamine (15.33 mmol, 2.131 ml, 1.552 g) and cyclophos (50 wgt % solution in EtOAc) (9.20 mmol, 2.74 ml, 2.93 g). The mixture was stirred at ambient temperature overnight then cyclophos (50 wgt % solution in EtOAc) (0.5 ml) added and the mixture stirred for a further 1 hr. The mixture was diluted with DCM (10 ml), washed with 2 N HCl (20 ml) then 2 N NaOH (20 ml), dried over Na$_2$SO$_4$, filtered and concentrated under reduced pressure to afford N-benzyl-3-chloro-N-(2-methylallyl)-1,2-dihydrocyclobutabenzene-1-carboxamide as a brown oil (1.8 g).

1.4 Preparation of trans-2-benzyl-6-chloro-3a-methyl-2,3,3a,4,5,9b-hexahydro-1H-benzo[e]isoindol-1-one and cis-2-benzyl-6-chloro-3a-methyl-2,3,3a,4, 5,9b-hexahydro-1H-benzo[e]isoindol-1-one

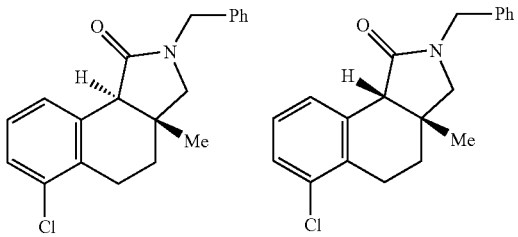 [SMILES: C[C@@]12CCc3c(Cl)cccc3[C@H]1C(=O)N(Cc1ccccc1)C2 ; C[C@@]12CCc3c(Cl)cccc3[C@@H]1C(=O)N(Cc1ccccc1)C2]

A solution of N-benzyl-3-chloro-N-(2-methylallyl)-1,2-dihydrocyclobutabenzene-1-carboxamide (5.52 mmol, 1.8 g) in bromobenzene (21 ml) was irradiated in a microwave for 30 min at 210 degrees. The bromobenzene was removed under reduced pressure and then purified by flash chromatographed using ethyl acetate in heptane (10 to 20%) to afford trans-2-benzyl-6-chloro-3a-methyl-2,3,3a,4,5,9b-hexahydro-1H-benzo[e]isoindol-1-one (221 mg, 12% yield), followed by cis-2-benzyl-6-chloro-3a-methyl-2,3,3a,4,5,9b-hexahydro-1H-benzo[e]isoindol-1-one (649 mg, 36% yield).

1.5 Preparation of cis-2-benzyl-6-chloro-3a-methyl-2,3,3a,4,5,9b-hexahydro-1H-benzo[e]isoindole

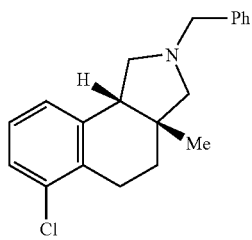 [SMILES: C[C@@]12CCc3c(Cl)cccc3[C@@H]1CN(Cc1ccccc1)C2]

To a solution of cis-2-benzyl-6-chloro-3a-methyl-2,3,3a,4,5,9b-hexahydro-1H-benzo[e]isoindol-1-one (1.992 mmol, 0.649 g) in THF (35 ml) was added borane methyl sulphide complex (13.94 mmol, 1.341 ml, 1.059 g). The mixture was stirred at 85° C. for 5 h then cooled to room temp and 5N HCl (11 ml) added portionwise over 10 min. The mixture was stirred under reflux for further 1.5 h then allowed to stand overnight. The mixture was basified to pH14 using 4N NaOH. This formed 2 layers, which were separated. The aqueous was further extracted with EtOAc and the combined organics washed with brine, dried ($Na_2SO_4$) and concentrated in vacuo to afford a residue (1.19 g). Flash chromatography of the residue using silica and diethyl ether in heptane (40 to 60%) as the eluent afforded cis-2-benzyl-6-chloro-3a-methyl-2,3,3a,4,5,9b-hexahydro-1H-benzo[e]isoindole (260 mg).

1.6 cis-6-Chloro-3a-methyl-2,3,3a,4,5,9b-hexahydro-1H-benzo[e]isoindole

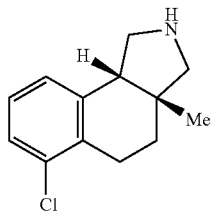 [SMILES: C[C@@]12CCc3c(Cl)cccc3[C@@H]1CNC2]

To a solution of cis-2-benzyl-6-chloro-3a-methyl-2,3,3a,4,5,9b-hexahydro-1H-benzo[e]isoindole (0.882 mmol, 0.275 g) in toluene (2 ml) was added 1-chloroethyl chloroformate (6.17 mmol, 0.883 g) and the reaction mixture was heated at 160° C. for 15 min in a microwave reactor. MeOH (2 ml) was added and the mixture further irradiated at 160° C. for 5 mins. The mixture was concentrated in vacuo and then diluted with water and extracted with DCM (3×). The combined organics were dried over $Na_2SO_4$ and concentrated in vacuo to afford a residue that was purified by silica column chromatography (eluting with DCM—20% MeOH in DCM) to afford cis-6-chloro-3a-methyl-2,3,3a,4,5,9b-hexahydro-1H-benzo[e]isoindole (163 mg), m/z=222.0 $[M+H]^+$.

EXAMPLE 2 trans-6-Chloro-3a-methyl-2,3,3a,4,5,9b-hexahydro-H-benzo[e]isoindole

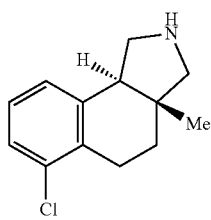 [SMILES: C[C@@]12CCc3c(Cl)cccc3[C@H]1CNC2]

trans-6-Chloro-3a-methyl-2,3,3a,4,5,9b-hexahydro-1H-benzo[e]isoindole was prepared according to procedure 1.5 to 1.6 starting with trans-2-benzyl-6-chloro-3a-methyl-2,3,3a,4,5,9b-hexahydro-1H-benzo[e]isoindol-1-one m/z=222.0 $[M+H]^+$.

EXAMPLE 3 cis-6-Bromo-3a-methyl-2,3,3a,4,5,9b-hexahydro-1H-benzo[e]isoindole hydrochloride

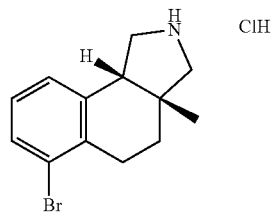

3.1 Preparation of 3-bromo-1,2-dihydrocyclobutabenzene-1-carboxylic acid

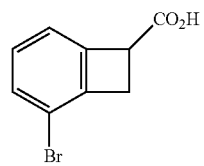 [SMILES: O=C(O)C1Cc2c(Br)cccc21]

Using 2,6-dibromobenzaldehyde, the 3-bromo-1,2-dihydrocyclobutabenzene-1-carboxylic acid was prepared using similar procedures as those in Example 1.1.1 to 1.1.5.

3.2 Preparation of cis-6-bromo-3a-methyl-2,3,3a,4,5,9b-hexahydro-H-benzo[e]isoindole

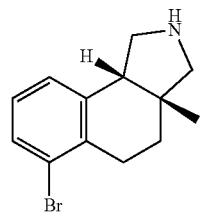

Similar protocols to procedures in protocol 1.3-1.6 were employed, using 3-bromo-1,2-dihydrocyclobutabenzene-1-carboxylic acid to afford cis-6-bromo-3a-methyl-2,3,3a,4,5,9b-hexahydro-1H-benzo[e]isoindole, m/z=266.0 $[M+H]^+$.

EXAMPLE 4 trans-6-Bromo-3a-methyl-2,3,3a,4,5,9b-hexahydro-1H-benzo[e]isoindole

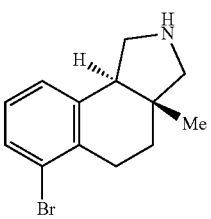 [SMILES: C[C@@]12CCc3c(Br)cccc3[C@H]1CNC2]

Using 3-bromo-1,2-dihydrocyclobutabenzene-1-carboxylic acid, the procedures in protocols 1.3-1.6 were employed to afford trans-6-Bromo-3a-methyl-2,3,3a,4,5,9b-hexahydro-1H-benzo[e]isoindole, m/z=266.0 [M+H]⁺.

EXAMPLE 5 cis-2-Benzyl-3a-methyl-6-((Z)-prop-1-enyl)-2,3,3a,4,5,9b-hexahydro-1H-benzo[e]isoindole)

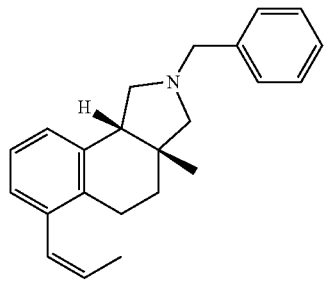 [SMILES: C/C=C\c1cccc2c1CC[C@@]1(C)CN(Cc3ccccc3)C[C@@H]21]

Tetrakis(triphenylphosphine)Pd(0) (0.021 mmol, 24.32 mg) was added in one portion to a mixture of cis-2-benzyl-6-bromo-3a-methyl-2,3,3a,4,5,9b-hexahydro-1H-benzo[e]isoindole (0.421 mmol, 150 mg) and (Z)-prop-1-enylboronic acid (0.631 mmol, 54.2 mg) in 2 N aq Na₂CO₃ (1 ml), DME (1 ml) and EtOH (0.5 ml) The reaction mixture was heated under microwave irradiation at 160° C. for 900 seconds and then the mixture was filtered through celite. The resulting filtrate was diluted with water and extracted with DCM (3×). The combined organic extracts were dried over Na₂SO₄ and conc in vauco to afford a brown oil that was purified by silica column chromatography (eluting with 10% EtOAc in heptane) to afford cis-2-benzyl-3a-methyl-6-((Z)-prop-1-enyl)-2,3,3a,4,5,9b-hexahydro-1H-benzo[e]isoindole) (127 mg), m/z: 318.3 [M+H]⁺.

EXAMPLE 6 cis-3a-Methyl-6-((Z)-prop-1-enyl)-2,3,3a,4,5,9b-hexahydro-1H-benzo[e]isoindole hydrochloride

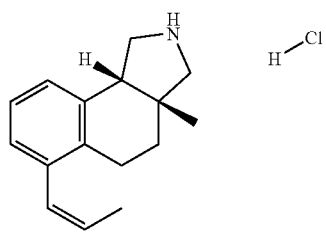 [SMILES: C/C=C\c1cccc2c1CC[C@@]1(C)CNC[C@@H]21 ; Cl]

cis-2-Benzyl-3a-methyl-6-((Z)-prop-1-enyl)-2,3,3a,4,5,9b-hexahydro-1H-benzo[e]isoindole (0.372 mmol, 118 mg) was dissolved in toluene (1 ml) and ACE-Cl (2.60 mmol, 0.286 ml, 372 mg) was added. The reaction mixture was heated to 160° C. for 15 minutes and then MeOH (1 ml) was added and the reaction mixture was heated to 160° C. for a further 5 minutes and then passed through an SCX cartridge and the resulting filtrate was purified by silica column chromatography (eluting with DCM—2, 4, 8, 16% MeOH(NH3)/DCM) The pure fractions were concentrated in vacuo and then 2 N HCl in MeOH added. The resulting solution was concentrated in vacuo to afford cis-3a-methyl-6-((Z)-prop-1-enyl)-2,3,3a,4,5,9b-hexahydro-1H-benzo[e]isoindole hydrochloride (85 mg): m/z: 228.1 [M+H]⁺.

EXAMPLE 7 cis-3a-Methyl-6-propyl-2,3,3a,4,5,9b-hexahydro-1H-benzo[e]isoindole hydrochloride

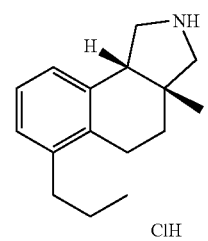 [SMILES: CCCc1cccc2c1CC[C@@]1(C)CNC[C@@H]21 ; Cl]

cis-3a-Methyl-6-((Z)-prop-1-enyl)-2,3,3a,4,5,9b-hexahydro-1H-benzo[e]isoindole hydrochloride (0.352 mmol, 80 mg) was dissolved in EtOH (2 ml) and palladium (5% on carbon) (0.035 mmol, 3.74 mg) was added. The resulting suspension was stirred under an atmosphere of hydrogen (balloon) for 72 h. Acetic acid (1 ml) and further palladium (5% on carbon) (0.035 mmol, 3.74 mg) was added and the reaction mixture left to stir for further 2 hours and then filtered through dicalite. The filtrate was concentrated in vacuo and the resulting crude residue was passed through an SCX cartridge and then purified by silica column chromatography (eluting with DCM—16% (2 N NH₃ in MeOH)/DCM)). The pure fractions were concentrated in vacuo and then dissolved in DCM (1 ml) and 2N HCl in ether added. The resulting solution was concentrated in vacuo to afford cis-3a-methyl-6-propyl-2,3,3a,4,5,9b-hexahydro-1H-benzo[e]isoindole hydrochloride 27 mg. m/z: 230.1 [M+H]⁺.

EXAMPLE 8 cis-2-Benzyl-3a-methyl-6-(prop-1-en-2-yl)-2,3,3a,4,5,9b-hexahydro-1H-benzo[e]isoindole

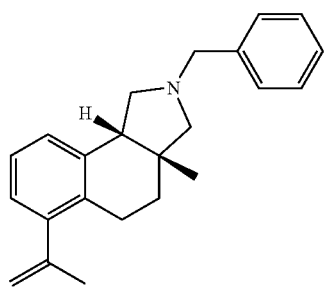 [SMILES: C=C(C)c1cccc2c1CC[C@@]1(C)CN(Cc3ccccc3)C[C@@H]21]

Similar protocols to procedures in example 5 were employed, using cis-2-benzyl-6-bromo-3a-methyl-2,3,3a,4,5,9b-hexahydro-H-benzo[e]isoindole and 4,4,5,5-tetramethyl-2-(prop-1-en-2-yl)-1,3,2-dioxaborolane to afford cis- 2-benzyl-3a-methyl-6-(prop-1-en-2-yl)-2,3,3a,4,5,9b-hexahydro-1H-benzo[e]isoindole, m/z=318.2 [M+H]⁺.

EXAMPLE 9 cis-3a-Methyl-6-(prop-1-en-2-yl)-2,3,3a,4,5,9b-hexahydro-H-benzo[e]isoindole hydrochloride

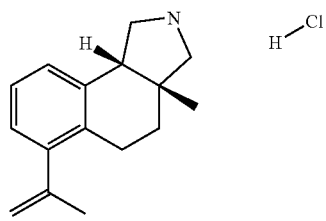 [SMILES: C=C(C)c1cccc2c1CC[C@@]1(C)CNC[C@@H]21 ; Cl]

Similar protocols to procedures in example 6 were employed, using cis-2-benzyl-3a-methyl-6-(prop-1-en-2-yl)-2,3,3a,4,5,9b-hexahydro-1H-benzo[e]isoindole to afford cis-3a-methyl-6-(prop-1-en-2-yl)-2,3,3a,4,5,9b-hexahydro-1H-benzo[e]isoindole hydrochloride, m/z=228.2 [M+H]⁺.

EXAMPLE 10 cis-2-Benzyl-6-cyclopropyl-3a-methyl-2,3,3a,4,5,9b-hexahydro-1H-benzo[e]isoindole

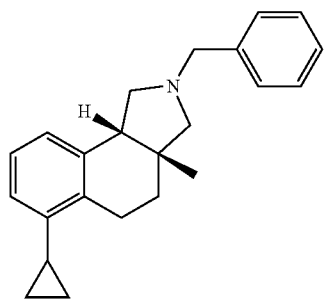 [SMILES: C[C@@]12CCc3c(C4CC4)cccc3[C@@H]1CN(Cc1ccccc1)C2]

cis-2-Benzyl-6-bromo-3a-methyl-2,3,3a,4,5,9b-hexahydro-1H-benzo[e]isoindole (0.421 mmol, 150 mg) was dissolved in dioxane (2 ml) and water (0.7 ml). Cyclopropylboronic acid (0.631 mmol, 54.2 mg), 1,1'-bis(diphenylphosphino)ferrocenedichloropalladium(II) (0.021 mmol, 15.40 mg) and potassium carbonate (0.631 mmol, 87 mg) were added and the reaction mixture was irradiated at 160° C. in a microwave reactor for 30 minutes. The reaction mixture was diluted with DCM and water. The phases were separated and DCM extract was concentrated in vacuo to give a crude residue that was purified by silica column chromatography (eluting with 10% EtOAc in heptane) to afford cis-2-benzyl-6-cyclopropyl-3a-methyl-2,3,3a,4,5,9b-hexahydro-1H-benzo[e]isoindole (75 mg), m/z: 318.2 [M+H]⁺.

EXAMPLE 11 cis-6-Cyclopropyl-3a-methyl-2,3,3a,4,5,9b-hexahydro-1H-benzo[e]isoindole hydrochloride

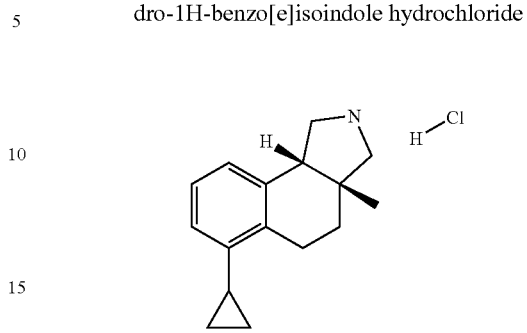

cis-2-Benzyl-6-cyclopropyl-3a-methyl-2,3,3a,4,5,9b-hexahydro-1H-benzo[e]isoindole (0.359 mmol, 75 mg) was dissolved in toluene (1 ml). ACE-Cl (1.654 mmol, 182 µl) was added and the reaction mixture; was heated in a microwave reactor at 160° C. for 15 minutes. MeOH (1 ml) was added and the mixture was again heated in a microwave reactor at 160° C. for 5 minutes. The resulting mixture was passed through an SCX cartridge and the resulting filtrate was concentrated in vacuo to give a crude residue that was purified by preparative-HPLC. To the pure fractions was added HCl in ether (1 ml) and the resulting solution was concentrated in vacuo to afford cis-6-cyclopropyl-3a-methyl-2,3,3a,4,5,9b-hexahydro-1H-benzo[e]isoindole hydrochloride (8.8 mg), m/z: 228.2 [M+H]⁺.

EXAMPLE 12 trans-2-Benzyl-3a-methyl-6-(prop-1-en-2-yl)-2,3,3a,4,5,9b-hexahydro-1H-benzo[e]isoindole

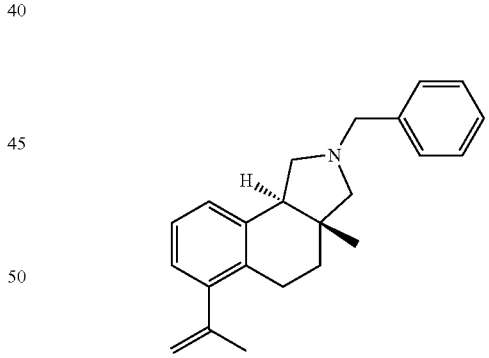

trans-2-Benzyl-6-bromo-3a-methyl-2,3,3a,4,5,9b-hexahydro-1H-benzo[e]isoindole (0.561 mmol, 200 mg) was dissolved in DME (1 ml) and Ethanol (0.5 ml). 2 N sodium carbonate solution (1 ml) was added along with 4,4,5,5-tetramethyl-2-(prop-1-en-2-yl)-1,3,2-dioxaborolane (0.842 mmol, 141 mg) and tetrakis(triphenylphosphine)Pd(0) (0.028 mmol, 32.4 mg). The reaction mixture was heated at 160° C. for 15 minutes in a microwave reactor and then diluted with water. The resulting mixture was extracted with DCM and the combined organic extracts were concentrated in vacuo to give a crude residue that was purified by silica column chromatography (eluting with 10% EtOAc in heptane) to afford trans-2-benzyl-3a-methyl-6-(prop-1-en-2-yl)-2,3,3a,4,5,9b-hexahydro-1H-benzo[e]isoindole (134 mg), m/z: 318.2 [M+H]⁺.

EXAMPLE 13 trans-3a-Methyl-6-(prop-1-en-2-yl)-2,3,3a,4,5,9b-hexahydro-H-benzo[e]isoindole hydrochloride

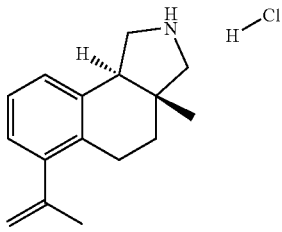

trans-2-Benzyl-3a-methyl-6-(prop-1-en-2-yl)-2,3,3a,4,5,9b-hexahydro-1H-benzo[e]isoindole (0.359 mmol, 134 mg) was dissolved in toluene (1 ml). ACE-Cl (2.95 mmol, 325 μl) was added and the reaction mixture was heated in a microwave reactor at 160° C. for 15 minutes. MeOH (1 ml) was added and the mixture was again heated in a microwave reactor at 160° C. for 5 minutes. The resulting mixture was passed through an SCX cartridge and the resulting filtrate was concentrated in vacuo to give a crude residue that was purified by preparative-HPLC. To the pure fractions was added HCl in ether (1 ml) and the resulting solution was concentrated in vacuo to afford trans-3a-methyl-6-(prop-1-en-2-yl)-2,3,3a,4,5,9b-hexahydro-1H-benzo[e]isoindole hydrochloride (41 mg), MS m/z: 228.1 [M+H]⁺.

EXAMPLE 14 trans-2-Benzyl-3a-methyl-6-((Z)-prop-1-enyl)-2,3,3a,4,5,9b-hexahydro-H-benzo[e]isoindole

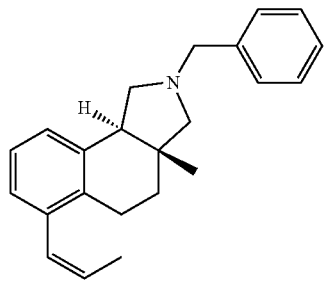 [SMILES: C/C=C\c1cccc2c1CC[C@@]1(C)CN(Cc3ccccc3)C[C@H]21]

trans-2-Benzyl-6-bromo-3a-methyl-2,3,3a,4,5,9b-hexahydro-1H-benzo[e]isoindole (0.561 mmol, 200 mg) was dissolved in DME (1 ml) and ethanol (0.5 ml). 2 N sodium carbonate solution (1 ml) was added along with (Z)-prop-1-enylboronic acid (0.842 mmol, 72.3 mg) and tetrakis(triphenylphosphine)Pd(0) (0.028 mmol, 32.4 mg). The reaction mixture was heated to 160° C. for 15 minutes in a microwave reactor and then diluted with water. The resulting mixture was extracted with DCM (3×) and the combined organic extracts were dried over Na₂SO₄ and concentrated in vacuo to afford a crude residue that was purified by silica column chromatography (eluting with 10% EtOAc in heptane) to afford trans-2-benzyl-3a-methyl-6-((Z)-prop-1-enyl)-2,3,3a,4,5,9b-hexahydro-1H-benzo[e]isoindole (120 mg), m/z: 318.2 [M+H]⁺.

EXAMPLE 15 trans-3a-Methyl-6-((Z)-prop-1-enyl)-2,3,3a,4,5,9b-hexahydro-1H-benzo[e]isoindole hydrochloride

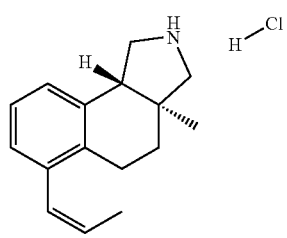

trans-2-Benzyl-3a-methyl-6-((Z)-prop-1-enyl)-2,3,3a,4,5,9b-hexahydro-1H-benzo[e]isoindole (0.378 mmol, 120 mg) was dissolved in toluene (1 ml) and ACE-Cl (2.65 mmol, 291 μl) was added. The reaction mixture was heated to 160° C. for 15 minutes in a microwave reactor then MeOH (1 ml) was added. The reaction mixture was again heated in a microwave reactor at 160° C. for 5 minutes and the resulting solution was passed through an SCX cartridge and then purified by prep-HPLC. HCl in ether (1 ml) was added to the purified fractions before removal of solvent in vacuo to afford trans-3a-methyl-6-((Z)-prop-1-enyl)-2,3,3a,4,5,9b-hexahydro-1H-benzo[e]isoindole hydrochloride (13.6 mg), m/z: 228.1 [M+H]⁺.

EXAMPLE 16 cis-2-Benzyl-3a-methyl-6-vinyl-2,3,3a,4,5,9b-hexahydro-1H-benzo[e]isoindole

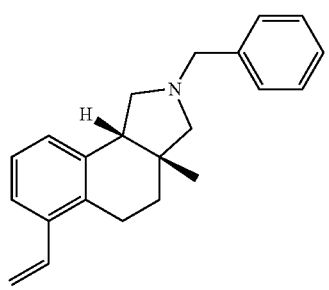 [SMILES: C=Cc1cccc2c1CC[C@@]1(C)CN(Cc3ccccc3)C[C@@H]21]

cis-2-Benzyl-6-bromo-3a-methyl-2,3,3a,4,5,9b-hexahydro-1H-benzo[e]isoindole (0.421 mmol, 150 mg) was dissolved in DME (1 ml) and ethanol (0.5 ml). 2 N sodium carbonate solution (1 ml), tetrakis(triphenylphosphine)Pd(0) (0.021 mmol, 24.32 mg) and 2,4,6-trivinyl-1,3,5,2,4,6-trioxatriborinane-pyridine complex (0.631 mmol, 152 mg) were added and the reaction mixture was heated at 160° C. for 15 minutes in a microwave reactor. The reaction mixture was diluted with water and extracted with DCM (3×). The combined organic extracts were concentrated in vacuo and then purified by silica column chromatography (eluting with 10% EtOAc in heptane) to afford cis-2-benzyl-3a-methyl-6-vinyl-2,3,3a,4,5,9b-hexahydro-1H-benzo[e]isoindole (100 mg). m/z: 304.2 [M+H]⁺.

EXAMPLE 17

(3aR*,4S*,9bS*)-6-Chloro-3a,4-dimethyl-2,3,3a,4,5,9b-hexahydro-H-benzo[e]isoindole hydrochloride

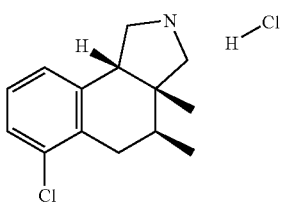

17.1 Preparation of (E)-N-benzyl-2-methylbut-2-en-1-amine

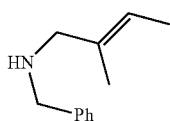

Benzylamine (18.66 mmol, 2.041 ml, 2 g) was dissolved in DCM (12.00 ml). (E)-2-methylbut-2-enal (18.66 mmol, 1.803 ml, 1.570 g) and magnesium sulfate (37.3 mmol, 4.49 g) were added and the reaction mixture was stirred at room temperature for 18 hours. The resulting suspension was filtered, washing with MeOH (30 ml). The filtrate was cooled to 0° C. and sodium tetrahydroborate (93 mmol, 3.53 g) was added portionwise and the reaction mixture was then warmed to room temperature and stirred for an additional 2 hours. The reaction mixture was then acidified with 5 N HCl and organic solvents removed in vacuo. The pH was adjusted to 1 using 5 N HCl and the aqueous solution was washed with ether before addition of 4N NaOH to pH 14. The aqueous solution was then extracted with DCM (3×). The combined DCM extracts were dried over MgSO₄, filtered and concentrated in vacuo to give (E)-N-benzyl-2-methylbut-2-en-1-amine (990 mg). ¹H NMR (400 MHz, CDCl₃) ppm 7.36-7.15 (5H, m, 5×ArH), 5.45 (1H, q, J=8 alkenyl CH), 3.73 (2H, s, CH₂), 3.16 (2H, s, CH₂), 1.66 (3H, s, CH₃), 1.62 (3H, d, J=8, CH₃).

17.2 Preparation of (E)-N-benzyl-3-chloro-N-(2-methylbut-2-enyl)-1,2-dihydrocyclobutabenzene-1-carboxamide

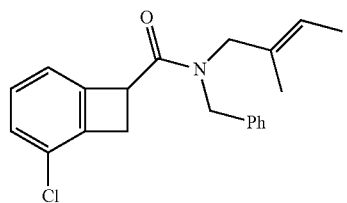 [SMILES: C/C=C(\C)CN(Cc1ccccc1)C(=O)C1Cc2c(Cl)cccc21]

3-Chloro-1,2-dihydrocyclobutabenzene-1-carboxylic acid (3.78 mmol, 690 mg) was dissolved in DCM (10 ml). (E)-N-benzyl-2-methylbut-2-en-1-amine (5.67 mmol, 993 mg) and triethylamine (7.56 mmol, 1.050 ml, 765 mg) were added, followed by cyclophos 50% in ethyl acetate (4.53 mmol, 2.70 ml, 2886 mg). The reaction mixture was stirred overnight at room temperature and then diluted with DCM (5 ml) and washed in turn with 2 N HCl (10 ml), 2 N NaOH (10 ml) and brine (10 ml). The organic extracts were dried over MgSO₄, filtered and concentrated in vacuo to give a crude residue that was purified by silica column chromatography (eluting with heptane—50% ethyl acetate:heptane) to give (E)-N-benzyl-3-chloro-N-(2-methylbut-2-enyl)-1,2-dihydrocyclobutabenzene-1-carboxamide (430 mg). m/z: 340.5 [M+H]⁺.

17.3 Preparation of (3aR*,4S*,9bS*)-2-benzyl-6-chloro-3a,4-dimethyl-2,3,3a,4,5,9b-hexahydro-H-benzo[e]isoindol-1-one and (3aR*,4S*,9bR*)-2-benzyl-6-chloro-3a,4-dimethyl-2,3,3a,4,5,9b-hexahydro-1H-benzo[e]isoindol-1-one

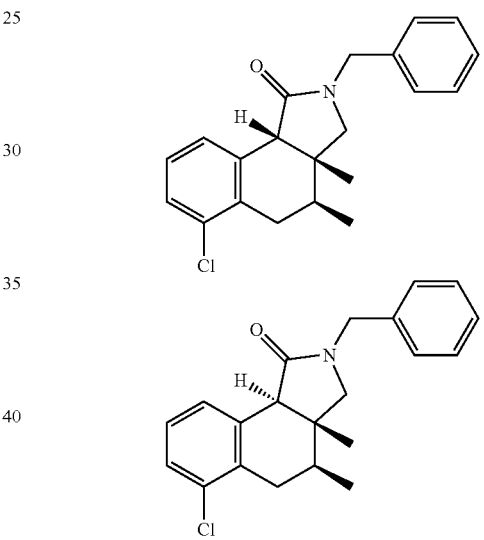

(E)-N-Benzyl-3-chloro-N-(2-methylbut-2-enyl)-1,2-dihydrocyclobutabenzene-1-carboxamide (0.971 mmol, 330 mg) was dissolved in bromobenzene (6 ml) and heated in a microwave reactor at 190° C. for 1 hour. The solvent was removed in vacuo and the resulting residue was purified by silica column chromatography (eluting with heptane then 5-20% ethyl acetate in heptane) to give (3aR*,4S*,9bR*)-2-benzyl-6-chloro-3a,4-dimethyl-2,3,3a,4,5,9b-hexahydro-1H-benzo[e]isoindol-1-one (229 mg) ¹H NMR (400 MHz, CDCl₃) ppm 7.42 (1H, d, ArH), 7.33-7.22 (7H, m, ArH), 4.57 (1H, d, CHHPh), 4.34 (1H, d, CHHPh), 3.34 (1H, s, CH), 3.24 (1H, d, CH), 3.01 (1H, d, CH), 2.90 (1H, dd, CH), 2.38 (1H, dd, CH), 1.77 (1H, m, CH), 1.04 (3H, s, CH₃), 0.91 (3H, d, CH₃) and (3aR*,4S*,9bS*)-2-benzyl-6-chloro-3a,4-dimethyl-2,3,3a,4,5,9b-hexahydro-H-benzo[e]isoindol-1-one (96 mg) ¹H NMR (400 MHz, CDCl₃) ppm 8.36 (1H, d, ArH), 7.45-7.13 (7H, m, 7×ArH), 4.55 (1H, d, CHHPh), 4.47 (1H, d, CHHPh), 3.40 (1H, s, CH), 3.07-2.94 (3H, m, 3×CH), 2.40 (1H, dd, CH), 2.21-2.10 (1H, m, CH₂), 0.99 (3H, d, CH₃), 0.68 (3H, s, CH₃).

17.4 Preparation of (3aR*,4S*,9bS*)-2-benzyl-6-chloro-3a,4-dimethyl-2,3,3a,4,5,9b-hexahydro-H-benzo[e]isoindole

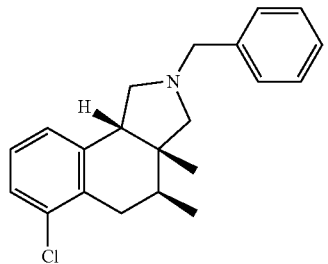 [SMILES: C[C@H]1Cc2c(Cl)cccc2[C@@H]2CN(Cc3ccccc3)C[C@]12C]

(3aR*,4S*,9bS*)-2-Benzyl-6-chloro-3a,4-dimethyl-2,3,3a,4,5,9b-hexahydro-1H-benzo[e]isoindol-1-one was dissolved in THF (1.3 ml). Borane THF (2 M solution) (2.82 mmol, 2.82 ml) was added and the reaction mixture was stirred at 70° C. overnight. MeOH and 5 N aqueous hydrochloric acid (4 ml) were added and the reaction mixture was stirred at 70° C. for a further 2 hours. The reaction mixture was then concentrated in vacuo to remove the organic solvents and then basified using 4 N NaOH. The aqueous mixture was extracted using DCM (×3) and the combined organic were dried over MgSO$_4$, filtered and concentrated in vacuo to give a crude residue that was purified by silica column chromatography (heptane—heptane: 30% ethyl acetate) to afford (3aR*,4S*,9bS*)-2-benzyl-6-chloro-3a,4-dimethyl-2,3,3a,4,5,9b-hexahydro-H-benzo[e]isoindole (49.8 mg). m/z: 326.3 [M+H]$^+$.

17.5 (3aR*,4S*,9bS*)-6-Chloro-3a,4-dimethyl-2,3,3a,4,5,9b-hexahydro-1H-benzo[e]isoindole hydrochloride

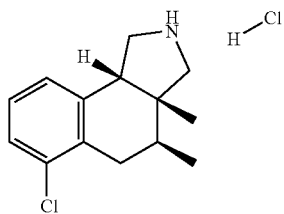

(3aR*,4S*,9bS*)-2-Benzyl-6-chloro-3a,4-dimethyl-2,3,3a,4,5,9b-hexahydro-1H-benzo[e]isoindole (0.153 mmol, 49.8 mg) was dissolved in toluene (1 ml). ACE-Cl (1.070 mmol, 0.118 ml, 153 mg) was added and the reaction mixture was heated in a microwave reactor at 160° C. for 15 minutes. Methanol (1 ml) was added and the reaction mixture was again heated in a microwave reactor at 160° C. for 5 minutes. The resulting solution was passed through an SCX cartridge and concentrated in vacuo to give a residue that was dissolved in 2 M HCl in MeOH and concentrated in vacuo to afford (3aR*,4S*,9bS*)-6-chloro-3a,4-dimethyl-2,3,3a,4,5,9b-hexahydro-1H-benzo[e]isoindole hydrochloride (27.5 mg). m/z: 236.1 [M+H]$^+$.

EXAMPLE 18

(3aR*,4S*,9bR*)-2-Benzyl-6-chloro-3a,4-dimethyl-2,3,3a,4,5,9b-hexahydro-1H-benzo[e]isoindole

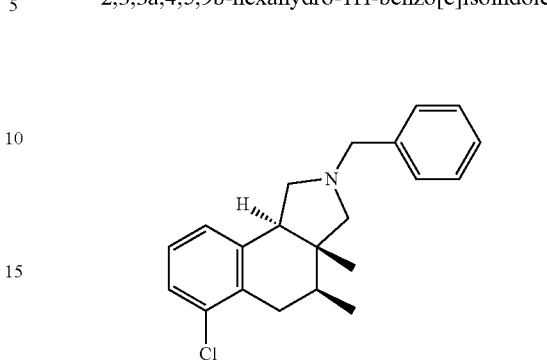

(3aR*,4S*,9bR*)-2-Benzyl-6-chloro-3a,4-dimethyl-2,3,3a,4,5,9b-hexahydro-1H-benzo[e]isoindol-1-one (229 mg, 0.674 mmol) was dissolved in THF (2.6 ml). Borane THF (2 M solution) (6.74 mmol, 6.74 ml) was added and the reaction mixture was heated to 70° C. overnight. MeOH and 5 N aq HCl (4 ml) were then added and the resulting solution was heated at 70° C. for a further 2 hours. The organic solvents were removed in vacuo and the reaction mixture was basified using 4 N NaOH. The aqueous mixture was extracted with DCM (×3) and the combined organic extracts were dried over magnesium sulphate, filtered and concentrated in vacuo to afford a residue that was purified by silica column chromatography (eluting with heptane—heptane: 30% ethyl acetate) to give (3aR*,4S*,9bR*)-2-benzyl-6-chloro-3a,4-dimethyl-2,3,3a,4,5,9b-hexahydro-1H-benzo[e]isoindole (52 mg). m/z: 326.3 [M+H]$^+$.

EXAMPLE 19

(3aR*,4S*,9bR*)-6-Chloro-3a,4-dimethyl-2,3,3a,4,5,9b-hexahydro-1H-benzo[e]isoindole hydrochloride

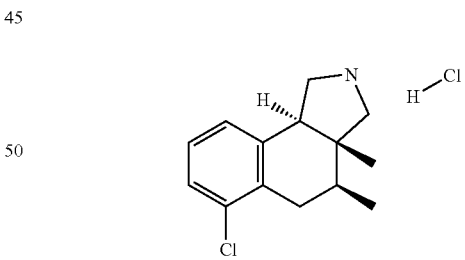

(3aR*,4S*,9bR*-2-Benzyl-6-chloro-3a,4-dimethyl-2,3,3a,4,5,9b-hexahydro-1H-benzo[e]isoindole (0.160 mmol, 52 mg) was dissolved in toluene (1 ml). ACE-Cl (1.117 mmol, 0.123 ml, 160 mg) was added and the reaction mixture was heated at 160° C. in a microwave reactor for 15 minutes. Methanol (1 ml) was then added and the mixture was heated in a microwave reactor at 160° C. for a further 5 minutes. The reaction mixture was passed through an SCX cartridge and the fractions containing the purified product were concentrated in vacuo to give a residue that was dissolved in 2 N HCl in MeOH. The resulting solution was concentrated in vacuo to afford (3aR*,4S*,9bR*)-6-chloro-3a,4-dimethyl-2,3,3a,4,5,9b-hexahydro-1H-benzo[e]isoindole hydrochloride (9.6 mg). m/z: 236.3 [M+H]⁺.

EXAMPLE 20 cis-6-(Difluoromethyl)-3a-methyl-2,3,3a,4,5,9b-hexahydro-1H-benzo[e]isoindole hydrochloride

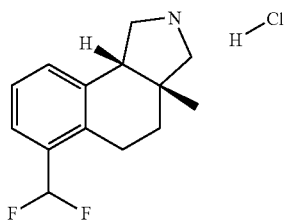

20.1 Preparation of cis-2-benzyl-3a-methyl-2,3,3a,4,5,9b-hexahydro-1H-benzo[e]isoindole-6-carbaldehyde

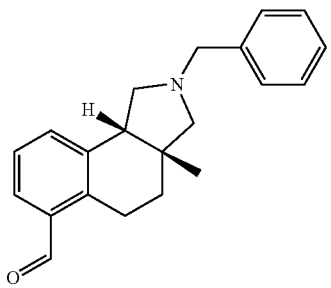 [SMILES: C[C@@]12CCc3c(C=O)cccc3[C@@H]1CN(Cc1ccccc1)C2]

cis-2-Benzyl-6-bromo-3a-methyl-2,3,3a,4,5,9b-hexahydro-1H-benzo[e]isoindole (0.561 mmol, 200 mg) was dissolved in THF (5 ml) and the resulting solution was cooled to −78° C. Butyllithium (2.5 M in hexanes)(2.81 mmol, 1.123 ml) was added dropwise and the reaction mixture was stirred at −78° C. for 30 minutes. N,N-Dimethylformamide (8.42 mmol, 0.777 ml, 734 mg) was added and the reaction mixture was stirred at −78° C. for a further 2 h and then quenched by the addition of saturated aqueous ammonium chloride solution and allowed to warm to room temperature. The resulting biphasic solution was separated and the aqueous phase was further extracted with ether (2×). The combined organic extracts were dried over magnesium sulphate, filtered and the solvent removed in vacuo. The crude product was purified by silica column chromatography (eluting with heptane—50:50 EtOAc:Heptane) to afford cis-2-benzyl-3a-methyl-2,3,3a,4,5,9b-hexahydro-1H-benzo[e]isoindole-6-carbaldehyde (95 mg), ¹H NMR (400 MHz, CDCl₃) ppm 10.29 (1H, s, CHO), 7.67-7.61 (1H, m, Ar—H), 3.62-3.55 (2H, m, NCH₂Ph), 3.32-3.04 (4H, m, 4×CH), 2.73 (1H, d, CH), 2.49 (1H, d, CH), 2.30 (1H, t, CH), 1.88-1.78 (1H, m, CH), 1.53-1.45 (1H, m, CH), 1.20 (3H, s, CH₃).

20.2 Preparation of cis-2-benzyl-6-(difluoromethyl)-3a-methyl-2,3,3a,4,5,9b-hexahydro-1H-benzo[e]isoindole

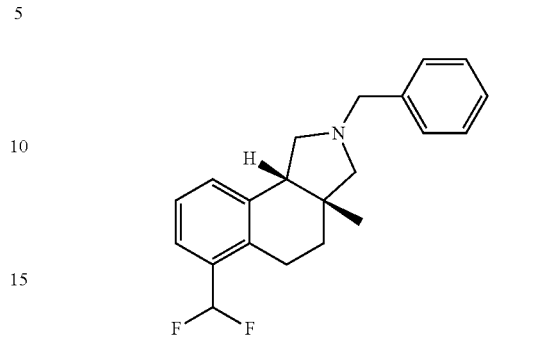

Deoxyfluor (50% solution in toluene) (3.11 mmol, 1376 μl) was added to cis-2-benzyl-3a-methyl-2,3,3a,4,5,9b-hexahydro-1H-benzo[e]isoindole-6-carbaldehyde (95 mg, 0.311 mmol) and the reaction mixture was stirred at room temperature for 18 h. The resulting solution was poured into ice/water and extracted with DCM. The aqueous layer was then neutralised with saturated sodium bicarbonate solution and extracted with DCM. The combined organics were then dried over magnesium sulphate, filtered and concentrated in vacuo to give a residue that was purified by silica column chromatography (eluting with 0-100% EtOAc in Heptane) to give cis-2-benzyl-6-(difluoromethyl)-3a-methyl-2,3,3a,4,5,9b-hexahydro-1H-benzo[e]isoindole (29 mg), ¹H NMR (400 MHz, CDCl₃) ppm 7.38-7.17 (8H, Ar—H), 6.78 (1H, t, CHF₂), 3.58 (2H, m, NCH₂Ph), 3.22 (1H, t, CH), 3.16 (1H, t, CH), 2.82 (1H, t, CH), 2.72 (1H, d, CH), 2.45 (1H, d, CH), 2.28 (1H, t, CH), 1.80 (1H, dd, CH), 1.49 (1H, dd, CH), 1.20 (3H, s, CH₃).

20.3 cis-6-(Difluoromethyl)-3a-methyl-2,3,3a,4,5,9b-hexahydro-1H-benzo[e]isoindole hydrochloride

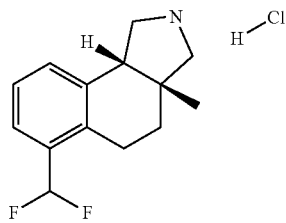

cis-2-Benzyl-6-(difluoromethyl)-3a-methyl-2,3,3a,4,5,9b-hexahydro-1H-benzo[e]isoindole (0.070 mmol, 23 mg) was dissolved in toluene (1 ml) and ACE-Cl (0.492 mmol, 0.054 ml, 70.3 mg) was added. The reaction mixture was heated to 160° C. for 15 minutes in a microwave reactor. MeOH (1 ml) was added and the reaction mixture was heated for a further 5 minutes at 160° C. in a microwave reactor and then the resulting solution was passed through an SCX cartridge. The fractions containing the desired product were concentrated in vacuo and then purified by silica column chromatography (eluting with DCM then 2-16% MeOH (NH3) in DCM) to give a crude residue that was dissolved in DCM and 2N HCl in ether (1 ml) was added. The solvent was removed in vacuo to afford cis-6-(difluoromethyl)₃a-methyl- 2,3,3a,4,5,9b-hexahydro-1H-benzo[e]isoindole hydrochloride (13 mg), m/z: 238.3 [M+H]⁺.

EXAMPLE 21 trans-6-(Difluoromethyl)-3a-methyl-2,3,3a,4,5,9b-hexahydro-1H-benzo[e]isoindole hydrochloride

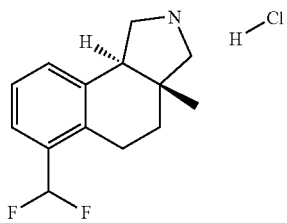

Similar protocols to procedures in example 20 were employed using trans-2-benzyl-6-bromo-3a-methyl-2,3,3a,4,5,9b-hexahydro-1H-benzo[e]isoindole to give trans-6-(difluoromethyl)-3a-methyl-2,3,3a,4,5,9b-hexahydro-1H-benzo[e]isoindole hydrochloride, m/z: 237.9 [M+H]⁺.

EXAMPLE 22 trans-6-Isopropyl-3a-methyl-2,3,3a,4,5,9b-hexahydro-1H-benzo[e]isoindole hydrochloride

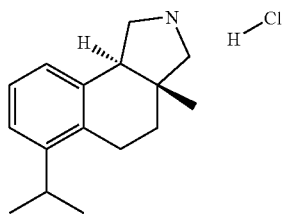

trans-3a-Methyl-6-(prop-1-en-2-yl)-2,3,3a,4,5,9b-hexahydro-1H-benzo[e]isoindole hydrochloride (41 mg, 0.137 mmol) was dissolved in ethanol (2 ml) and acetic acid (0.5 ml). 5% Pd on C (0.298 mg) was added and the reaction mixture was stirred under an atmosphere of H₂ (1 bar) for 18 h. The resulting suspension was filtered through celite and then passed through an SCX cartridge. The purified fractions were concentrated in vacuo and then dissolved in DCM (1 ml). 2 N HCl in Et₂O (1 ml) was added and the solvent was removed in vacuo to afford trans-6-Isopropyl-3a-methyl-2,3,3a,4,5,9b-hexahydro-1H-benzo[e]isoindole hydrochloride (43 mg), m/z: 230.3 [M+H]⁺.

EXAMPLE 23 trans-6-Cyclopropyl-3a-methyl-2,3,3a,4,5,9b-hexahydro-1H-benzo[e]isoindole hydrochloride

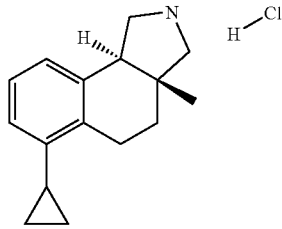

Similar protocols to procedures in examples 10 and 11 were employed using trans-2-benzyl-6-bromo-3a-methyl-2,3,3a,4,5,9b-hexahydro-1H-benzo[e]isoindole to give trans-6-cyclopropyl-3a-methyl-2,3,3a,4,5,9b-hexahydro-1H-benzo[e]isoindole hydrochloride, m/z: 228.1 [M+H]⁺.

EXAMPLE 24 cis-3a-Methyl-6-vinyl-2,3,3a,4,5,9b-hexahydro-1H-benzo[e]isoindole hydrochloride

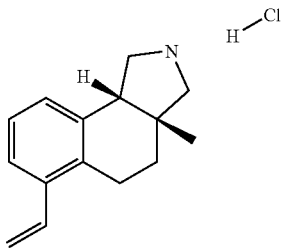 [SMILES: Cl ; C=Cc1cccc2c1CC[C@@]1(C)CNC[C@@H]21]

Similar protocols to procedures in example 6 were employed, using cis-2-benzyl-3a-methyl-6-vinyl-2,3,3a,4,5,9b-hexahydro-1H-benzo[e]isoindole to afford cis-3a-methyl-6-vinyl-2,3,3a,4,5,9b-hexahydro-1H-benzo[e]isoindole hydrochloride, m/z: 214.2 [M+H]⁺.

EXAMPLE 25 cis-6-Ethyl-3a-methyl-2,3,3a,4,5,9b-hexahydro-1H-benzo[e]isoindole hydrochloride

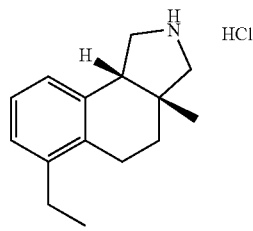 [SMILES: CCc1cccc2c1CC[C@@]1(C)CNC[C@@H]21 ; Cl]

Similar protocols to procedures in example 7 were employed, using cis-3a-methyl-6-vinyl-2,3,3a,4,5,9b-hexahydro-1H-benzo[e]isoindole hydrochloride to afford cis-6-ethyl-3a-methyl-2,3,3a,4,5,9b-hexahydro-1H-benzo[e]isoindole hydrochloride, m/z=216.3 [M+H]⁺.

EXAMPLE 26 trans-6,7-Dichloro-3a-methyl-2,3,3a,4,5,9b-hexahydro-1H-benzo[e]isoindole hydrochloride

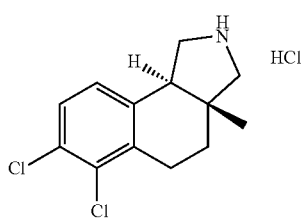 [SMILES: C[C@@]12CCc3c(ccc(Cl)c3Cl)[C@H]1CNC2 ; Cl]

26.1 Preparation of trans-2-benzyl-6,7-dichloro-3a-methyl-2,3,3a,4,5,9b-hexahydro-1H-benzo[e]isoindole

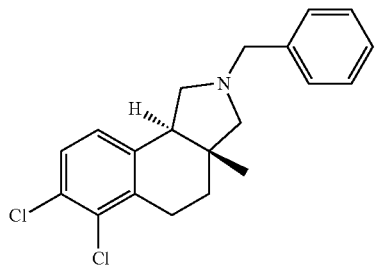 [SMILES: C[C@@]12CCc3c(ccc(Cl)c3Cl)[C@H]1CN(Cc1ccccc1)C2]

A mixture of trans-2-benzyl-7-bromo-6-chloro-3a-methyl-2,3,3a,4,5,9b-hexahydro-1H-benzo[e]isoindole (0.144 mmol, 56.4 mg) and nickel (II) chloride (0.289 mmol, 38.2 mg) in NMP (1 ml) was heated in microwave at 210° C. for 0.5 h. The reaction mixture was diluted with water, extracted with DCM and separated by hydrophobic frits. The filtrate was passed through a Strata SCX column (1 g) then concentrated to give brown residue that was purified by silica column chromatography (eluting with neat heptane to 2:1 heptane: EtOAc). The purified fractions were concentrated in vacuo and then passed through a Strata SCX column (1 g) to give trans-2-benzyl-6,7-dichloro-3a-methyl-2,3,3a,4,5,9b-hexahydro-1H-benzo[e]isoindole (34.6 mg), m/z=348.0, 350.0 [M+H]$^+$.

26.2 trans-6,7-Dichloro-3a-methyl-2,3,3a,4,5,9b-hexahydro-1H-benzo[e]isoindole hydrochloride

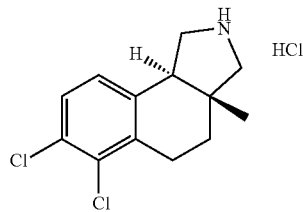 [SMILES: C[C@@]12CCc3c(ccc(Cl)c3Cl)[C@H]1CNC2 ; Cl]

Similar protocols to procedures in example 11 (using trans-2-benzyl-6,7-dichloro-3a-methyl-2,3,3a,4,5,9b-hexahydro-1H-benzo[e]isoindole) were employed to afford trans-6,7-dichloro-3a-methyl-2,3,3a,4,5,9b-hexahydro-1H-benzo[e]isoindole hydrochloride, m/z=258.0, 260.0 [M+H]$^+$.

EXAMPLE 27 cis-6,7-Dichloro-3a-methyl-2,3,3a,4,5,9b-hexahydro-1H-benzo[e]isoindole hydrochloride

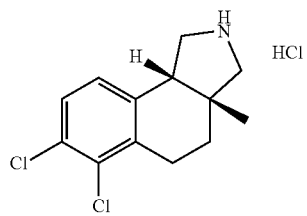 [SMILES: C[C@@]12CCc3c(ccc(Cl)c3Cl)[C@@H]1CNC2 ; Cl]

27.1 Preparation of cis-2-benzyl-6,7-dichloro-3a-methyl-2,3,3a,4,5,9b-hexahydro-1H-benzo[e]isoindole

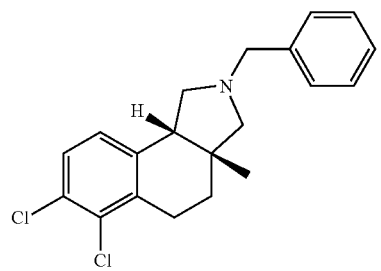 [SMILES: C[C@@]12CCc3c(ccc(Cl)c3Cl)[C@@H]1CN(Cc1ccccc1)C2]

Similar protocols to procedures in example 26.1 (using cis-2-benzyl-7-bromo-6-chloro-3a-methyl-2,3,3a,4,5,9b-hexahydro-1H-benzo[e]isoindole) were employed to afford cis-2-benzyl-6,7-dichloro-3a-methyl-2,3,3a,4,5,9b-hexahydro-1H-benzo[e]isoindole, m/z=348.0, 350.0 [M+H]$^+$.

27.2 cis-6,7-Dichloro-3a-methyl-2,3,3a,4,5,9b-hexahydro-1H-benzo[e]isoindole hydrochloride

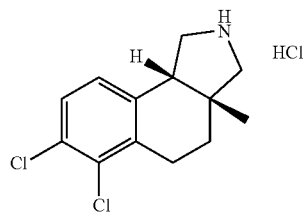 [SMILES: C[C@@]12CCc3c(ccc(Cl)c3Cl)[C@@H]1CNC2 ; Cl]

Similar protocols to procedures in example 11 (using cis-2-benzyl-6,7-dichloro-3a-methyl-2,3,3a,4,5,9b-hexahydro-1H-benzo[e]isoindole) were employed to afford cis-6,7-dichloro-3a-methyl-2,3,3a,4,5,9b-hexahydro-1H-benzo[e]isoindole hydrochloride, m/z=258.0, 260.0 [M+H]$^+$.

EXAMPLE 28

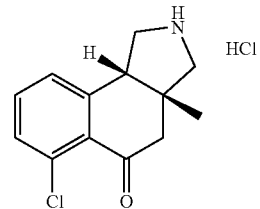 [SMILES: C[C@]12CNC[C@H]1c1cccc(Cl)c1C(=O)C2 ; Cl]

28.1 Preparation of cis-ethyl 6-chloro-3a-methyl-3,3a,4,5-tetrahydro-1H-benzo[e]isoindole-2(9bH)-carboxylate

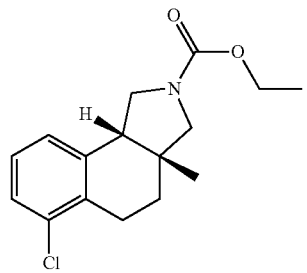 [SMILES: CCOC(=O)N1C[C@H]2c3cccc(Cl)c3CC[C@@]2(C)C1]

cis-2-Benzyl-6-chloro-3a-methyl-2,3,3a,4,5,9b-hexahydro-1H-benzo[e]isoindole (18.60 mmol, 5.8 g) was dissolved in toluene and heated to reflux. Ethyl carbonochloridate (55.8 mmol, 5.33 ml, 6.06 g) was added dropwise and the reaction mixture left to stir at reflux for 2 hours. TLC and mass spec showed no starting material. Solvent removed in vacuo and crude material purified by silica column chromatography (eluting with 0-30% ethyl acetate:heptane) to give cis-ethyl 6-chloro-3a-methyl-3,3a,4,5-tetrahydro-1H-benzo[e]isoindole-2(9bH)-carboxylate (4.89 g), m/z=294.3 [M+H]+.

28.2 Preparation of cis-ethyl 6-chloro-3a-methyl-5-oxo-3,3a,4,5-tetrahydro-1H-benzo[e]isoindole-2(9bH)-carboxylate

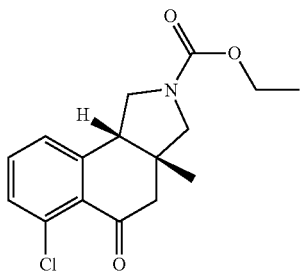 [SMILES: CCOC(=O)N1C[C@H]2c3cccc(Cl)c3C(=O)C[C@@]2(C)C1]

cis-Ethyl 6-chloro-3a-methyl-3,3a,4,5-tetrahydro-1H-benzo[e]isoindole-2(9bH)-carboxylate (5.55 mmol, 1630 mg) was dissolved in water (33 ml), acetic acid (8.25 ml) and 1,4-dioxane (8.25 ml). Cerium(IV) oxide (1.276 mmol, 220 mg) and sodium bromate (5.55 mmol, 837 mg) were added and the reaction mixture was heated to 95° C. for 3 hours. The reaction mixture was cooled to rt, diluted with water (30 ml) and extracted with ether. The organic extracts were dried over magnesium sulphate, filtered and the solvent removed in vacuo to give to give a crude residue that was purified by silica column chromatography (eluting with 0-60% ethyl acetate in heptane) to give cis-ethyl 6-chloro-3a-methyl-5-oxo-3,3a,4,5-tetrahydro-1H-benzo[e]isoindole-2(9bH)-carboxylate (673 mg), m/z=308.7 [M+H]+.

28.3 cis-6-Chloro-3a-methyl-2,3,3a,4-tetrahydro-1H-benzo[e]isoindol-5(9bH)-one hydrochloride

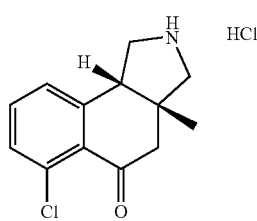 [SMILES: Cl ; C[C@]12CNC[C@H]1c1cccc(Cl)c1C(=O)C2]

cis-Ethyl 6-chloro-3a-methyl-5-oxo-3,3a,4,5-tetrahydro-1H-benzo[e]isoindole-2(9bH)-carboxylate (0.162 mmol, 50 mg) was dissolved in dichloromethane (1 ml). Iodotrimethylsilane (0.487 mmol, 0.070 ml, 98 mg) was added and the reaction mixture was heated to 100° C. for 30 minutes in the microwave. 2 N HCl in MeOH (2 ml) was added to the reaction mixture was stirred at rt for 20 minutes. The reaction mixture was then concentrated in vacuo and the residue was dissolved in 2 N HCl and washed with ether. The acidic extract was basified using 4 N NaOH and extracted with ether. The ether extract was then dried over magnesium sulphate, filtered and concentrated in vacuo to give a crude residue that was purified by basic prep-HPLC. The purified fractions were concentrated in vacuo and then redissolved in 2 N HCl in MeOH and concentrated in vacuo to give cis-6-chloro-3a-methyl-2,3,3a,4-tetrahydro-1H-benzo[e]isoindol-5(9bH)-one hydrochloride (2.4 mg), m/z=236.3 [M+H]+.

EXAMPLE 29

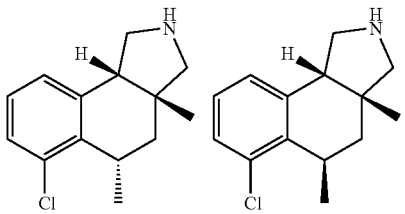

29.1 Preparation of cis-ethyl 6-chloro-3a-methyl-5-methylene-3,3a,4,5-tetrahydro-1H-benzo[e]isoindole-2(9bH)-carboxylate

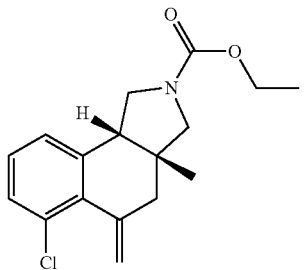

cis-Ethyl 6-chloro-3a-methyl-5-oxo-3,3a,4,5-tetrahydro-1H-benzo[e]isoindole-2(9bH)-carboxylate (4.87 mmol, 1.5 g) was dissolved in THF (50 ml).

Methyltriphenylphosphonium bromide (7.31 mmol, 2.61 g) was added, followed dropwise by potassium 2-methylpropan-2-olate (7.31 mmol, 7.31 ml). The reaction mixture was stirred at rt for 48 h and then saturated aqueous ammonium chloride was added. The reaction mixture was concentrated in vacuo to remove THF. The resulting mixture was diluted with water and extracted with EtOAc (3x). The combined organic extracts were dried over magnesium sulphate, filtered and the concentrated in vacuo to afford a crude mixture that was purified by silica column chromatography (eluting with heptane-50% ethyl acetate:heptane) to afford cis-ethyl 6-chloro-3a-methyl-5-methylene-3,3a,4,5-tetrahydro-1H-benzo[e]isoindole-2(9bH)-carboxylate (474 mg), m/z=306.2 [M+H]+.

29.2 Preparation of (3aR*,5S*,9bS*)-ethyl 6-chloro-3a,5-dimethyl-3,3a,4,5-tetrahydro-1H-benzo[e]isoindole-2(9bH)-carboxylate and (3aR*,5R*,9bS*)-ethyl 6-chloro-3a,5-dimethyl-3,3a,4,5-tetrahydro-1H-benzo[e]isoindole-2(9bH)-carboxylate

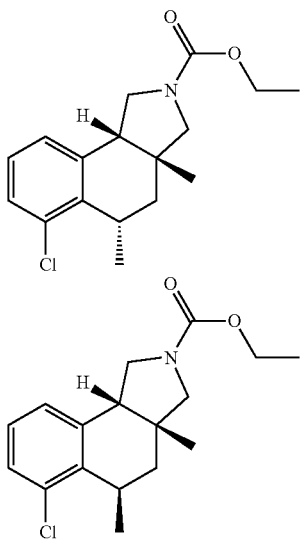

cis-Ethyl 6-chloro-3a-methyl-5-methylene-3,3a,4,5-tetrahydro-1H-benzo[e]isoindole-2(9bH)-carboxylate (0.245 mmol, 75 mg) was dissolved in Ethanol (7 ml). platinum(IV) oxide (0.025 mmol, 5.57 mg) was added and reaction mixture was stirred under a balloon of H$_2$ for 1 hour. The catalyst was removed by filtration and the resulting filtrate was concentrated in vacuo and purified by basic prep-LCMS to give a 1:1 inseparable mixture of (3aR*,5S*,9bS*)-ethyl 6-chloro-3a,5-dimethyl-3,3a,4,5-tetrahydro-1H-benzo[e]isoindole-2(9bH)-carboxylate and (3aR*,5R*,9bS*)-ethyl 6-chloro-3a,5-dimethyl-3,3a,4,5-tetrahydro-1H-benzo[e]isoindole-2(9bH)-carboxylate (36 mg), m/z=308.2 [M+H]$^+$.

29.3 (3aR*,5S*,9bS*)-6-Chloro-3a,5-dimethyl-2,3,3a,4,5,9b-hexahydro-1H-benzo[e]isoindole and (3aR*,5R*,9bS*)-6-chloro-3a,5-dimethyl-2,3,3a,4,5,9b-hexahydro-1H-benzo[e]isoindole

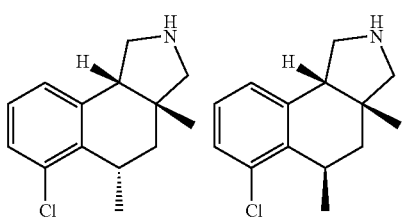

A 1:1 inseparable mixture of (3aR*,5S*,9bS*)-ethyl 6-chloro-3a,5-dimethyl-3,3a,4,5-tetrahydro-1H-benzo[e]isoindole-2(9bH)-carboxylate and (3aR*,5R*,9bS*)-ethyl 6-chloro-3a,5-dimethyl-3,3a,4,5-tetrahydro-1H-benzo[e]isoindole-2(9bH)-carboxylate (0.097 mmol, 30 mg) was dissolved in DCM (1 ml). Iodotrimethylsilane was added and the reaction mixture was heated to 100° C. for 30 minutes. 2 N HCl in MeOH (1 ml) was added and the reaction mixture was stirred at rt for 1 hour and then passed through an SCX cartridge to afford a 1:1 mixture of (3aR*,5S*,9bS*)-6-chloro-3a,5-dimethyl-2,3,3a,4,5,9b-hexahydro-1H-benzo[e]isoindole and (3aR*,5R*,9bS*)-6-chloro-3a,5-dimethyl-2,3,3a,4,5,9b-hexahydro-1H-benzo[e]isoindole (13 mg), m/z=236.2 [M+H]$^+$.

EXAMPLE 30 trans-2-Benzyl-7-bromo-6-chloro-3a-methyl-2,3,3a,4,5,9b-hexahydro-1H-benzo[e]isoindole

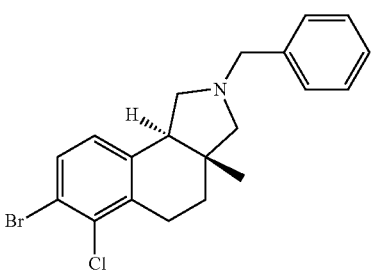

Similar protocols to procedures in example 17 and 18 (procedures 17.2 (using 3-chloro-4-bromo-1,2-dihydrocyclobutabenzene-1-carboxylic acid and N-benzyl-2-methyl-prop-2-en-1-amine)-17.3 and procedure 18) were employed to afford trans-2-benzyl-7-bromo-6-chloro-3a-methyl-2,3,3a,4,5,9b-hexahydro-1H-benzo[e]isoindole, m/z=406.0, 408.0 [M+H]$^+$.

EXAMPLE 31 trans-2-Benzyl-6-chloro-7-methoxy-3a-methyl-2,3,3a,4,5,9b-hexahydro-1H-benzo[e]isoindole

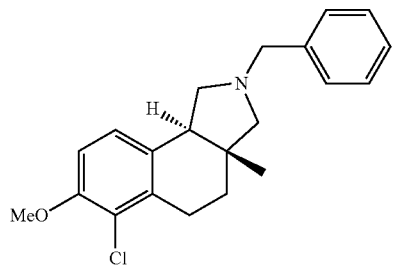 [SMILES: COc1ccc2c(c1Cl)CC[C@@]1(C)CN(Cc3ccccc3)C[C@H]21]

A mixture of trans-2-benzyl-7-bromo-6-chloro-3a-methyl-2,3,3a,4,5,9b-hexahydro-1H-benzo[e]isoindole (0.704 mmol, 275 mg), sodium methoxide (8.75 mmol, 2 ml, 1890 mg), copper(I) bromide (0.352 mmol, 51.5 mg) and ethyl acetate (0.699 mmol, 69 µl, 62.2 mg) in MeOH (2 ml) was heated in a microwave reactor at 120° C. for 0.5 h. The reaction mixture was partitioned between DCM and water and the aqueous was further extracted with DCM. The combined organic extracts were dried over Na$_2$SO$_4$ and concentrated in vacuo before being purified by silica column chromatography (eluting with neat DCM—5% MeOH in DCM)

to afford the trans-2-benzyl-6-chloro-7-methoxy-3a-methyl-2,3,3a,4,5,9b-hexahydro-1H-benzo[e]isoindole (26.4 mg), m/z=342.2, 344.2 [M+H]⁺.

EXAMPLE 32 cis-2-Benzyl-6-chloro-7-methoxy-3a-methyl-2,3,3a,4,5,9b-hexahydro-1H-benzo[e]isoindole

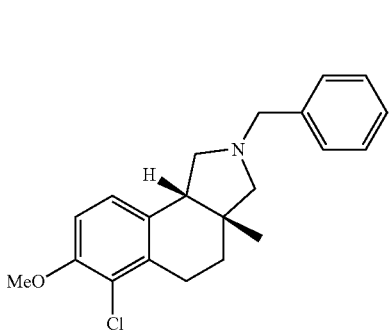 [SMILES: COc1ccc2c(c1Cl)CC[C@@]1(C)CN(Cc3ccccc3)C[C@@H]21]

Similar protocols to procedures in example 31 (using cis-2-benzyl-7-bromo-6-chloro-3a-methyl-2,3,3a,4,5,9b-hexahydro-1H-benzo[e]isoindole) were employed to afford cis-2-benzyl-7-bromo-6-chloro-3a-methyl-2,3,3a,4,5,9b-hexahydro-1H-benzo[e]isoindole, m/z=342.2, 344.2 [M+H]⁺.

EXAMPLE 33 cis-2-Benzyl-6-chloro-3a,7-dimethyl-2,3,3a,4,5,9b-hexahydro-1H-benzo[e]isoindole

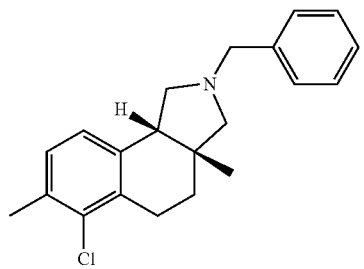 [SMILES: Cc1ccc2c(c1Cl)CC[C@@]1(C)CN(Cc3ccccc3)C[C@@H]21]

A mixture of cis-2-benzyl-7-bromo-6-chloro-3a-methyl-2,3,3a,4,5,9b-hexahydro-1H-benzo[e]isoindole (0.154 mmol, 60 mg), tetrakis(triphenylphosphine)Pd(0) (7.68 μmol, 8.96 mg), 2,4,6-trimethyl-1,3,5,2,4,6-trioxatriborinane (0.184 mmol, 52 μl, 46.3 mg) and potassium carbonate (0.230 mmol, 32.2 mg) in 1,4-Dioxane (1 ml) and Water (0.5 ml) was heated in a microwave reactor at 130° C. for 20 min. The reaction mixture was diluted with DCM and water, the phases were separated and the aqueous was extracted with DCM (using a hydrophobic frit). The combined organic extracts were concentrated in vacuo and purified by silica column chromatography (eluting with neat heptane—2:1 heptane:ethyl acetate). The fractions containing the product compound were concentrated in vacuo and then redissolved in MeOH and then passed through Strata SCX column (1 g) and concentrated in vacuo to afford cis-2-benzyl-6-chloro-3a,7-dimethyl-2,3,3a,4,5,9b-hexahydro-1H-benzo[e]isoindole (39.4 mg), m/z=326.2 [M+H]⁺.

EXAMPLE 34 trans-2-Benzyl-6-chloro-3a-methyl-7-vinyl-2,3,3a,4,5,9b-hexahydro-1H-benzo[e]isoindole

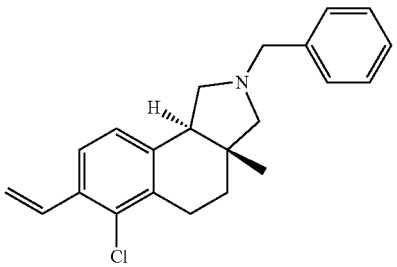 [SMILES: C=Cc1ccc2c(c1Cl)CC[C@@]1(C)CN(Cc3ccccc3)C[C@H]21]

Similar protocols to procedures in example 16 was employed, using trans-2-benzyl-7-bromo-6-chloro-3a-methyl-2,3,3a,4,5,9b-hexahydro-1H-benzo[e]isoindole to afford trans-2-benzyl-6-chloro-3a-methyl-7-vinyl-2,3,3a,4,5,9b-hexahydro-1H-benzo[e]isoindole, m/z=338.0, 340.2 [M+H]⁺.

EXAMPLE 35 cis-6-Chloro-3a,7-dimethyl-2,3,3a,4,5,9b-hexahydro-1H-benzo[e]isoindole

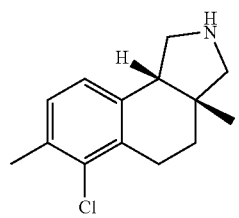

Similar protocols to procedures in example 1 (protocol 1.6) (using cis-2-benzyl-6-chloro-3a,7-dimethyl-2,3,3a,4,5,9b-hexahydro-1H-benzo[e]isoindole) were employed to afford cis-6-chloro-3a,7-dimethyl-2,3,3a,4,5,9b-hexahydro-1H-benzo[e]isoindole, m/z=236.0, 238.0 [M+H]⁺.

EXAMPLE 36 cis-6-Chloro-7-methoxy-3a-methyl-2,3,3a,4,5,9b-hexahydro-1H-benzo[e]isoindole

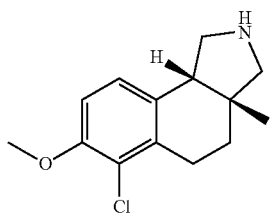

Similar protocols to procedures in example 1 (protocol 1.6) (using cis-2-benzyl-6-chloro-7-methoxy-3a-methyl-2,3,3a,4,5,9b-hexahydro-1H-benzo[e]isoindole) were employed to afford cis-6-chloro-3a,7-dimethyl-2,3,3a,4,5,9b-hexahydro-1H-benzo[e]isoindole, m/z=252.0 [M+H]⁺.

EXAMPLE 37 cis-6-Chloro-7-cyclopropyl-3a-methyl-2,3,3a,4,5,9b-hexahydro-1H-benzo[e]isoindole

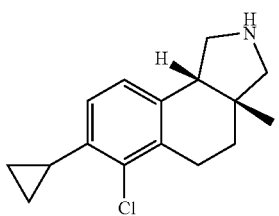 [SMILES: C[C@@]12CCc3c(ccc(C4CC4)c3Cl)[C@@H]1CNC2]

37.1 Preparation of cis-2-benzyl-7-bromo-6-chloro-3a-methyl-2,3,3a,4,5,9b-hexahydro-1H-benzo[e]isoindole

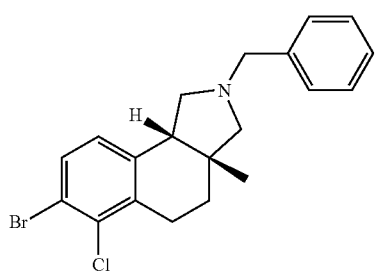

Similar protocols to procedures in example 17 (protocol 17.2, using 3-chloro-4-bromo-1,2-dihydrocyclobutabenzene-1-carboxylic acid N-benzyl-2-methylprop-2-en-1-amine to 17.4) were employed, to afford cis-2-benzyl-7-bromo-6-chloro-3a-methyl-2,3,3a,4,5,9b-hexahydro-1H-benzo[e]isoindole, m/z=390.0, 392.0 [M+H]⁺.

37.2 cis-6-Chloro-7-cyclopropyl-3a-methyl-2,3,3a,4,5,9b-hexahydro-1H-benzo[e]isoindole

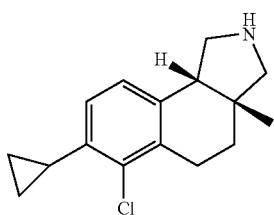 [SMILES: C[C@@]12CCc3c(ccc(C4CC4)c3Cl)[C@@H]1CNC2]

Similar protocols to procedures in example 10 and 11 (protocol 10 and 11) (using cis-2-benzyl-7-bromo-6-chloro-3a-methyl-2,3,3a,4,5,9b-hexahydro-1H-benzo[e]isoindole) were employed to afford cis-6-chloro-3a,7-dimethyl-2,3,3a,4,5,9b-hexahydro-1H-benzo[e]isoindole, m/z=262.0, 264.0 [M+H]⁺.

EXAMPLE 38 cis-6-Chloro-7-vinyl-3a-methyl-2,3,3a,4,5,9b-hexahydro-1H-benzo[e]isoindole hydrochloride

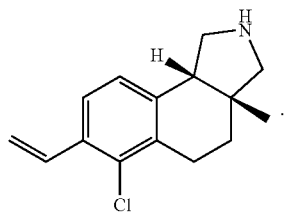 [SMILES: C=Cc1ccc2c(c1Cl)CC[C@@]1(C)CNC[C@@H]21]

38.1 Preparation of cis-2-benzyl-6-chloro-3a-methyl-7-vinyl-2,3,3a,4,5,9b-hexahydro-1H-benzo[e]isoindole

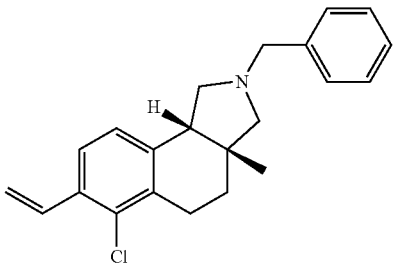 [SMILES: C=Cc1ccc2c(c1Cl)CC[C@@]1(C)CN(Cc3ccccc3)C[C@@H]21]

Similar protocols to procedures in example 16 (using cis-2-benzyl-7-bromo-6-chloro-3a-methyl-2,3,3a,4,5,9b-hexahydro-1H-benzo[e]isoindole and 2,4,6-trivinyl-1,3,5,2,4,6-trioxatriborinane-pyridine complex) were employed to afford cis-2-benzyl-6-chloro-3a-methyl-7-vinyl-2,3,3a,4,5,9b-hexahydro-1H-benzo[e]isoindole, m/z=338.2 [M+H]⁺.

38.2 cis-6-Chloro-7-vinyl-3a-methyl-2,3,3a,4,5,9b-hexahydro-1H-benzo[e]isoindole hydrochloride

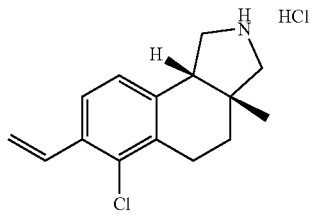 [SMILES: Cl ; C=Cc1ccc2c(c1Cl)CC[C@@]1(C)CNC[C@@H]21]

Similar protocols to procedures in example 19 (using cis-2-benzyl-6-chloro-3a-methyl-7-vinyl-2,3,3a,4,5,9b-hexahydro-1H-benzo[e]isoindole) were employed to afford cis-2- benzyl-6-chloro-3a-methyl-7-vinyl-2,3,3a,4,5,9b-hexahydro-1H-benzo[e]isoindole hydrochloride, m/z=248.2 [M+H]⁺.

EXAMPLE 39 cis-6-Chloro-7-ethyl-3a-methyl-2,3,3a,4,5,9b-hexahydro-1H-benzo[e]isoindole hydrochloride

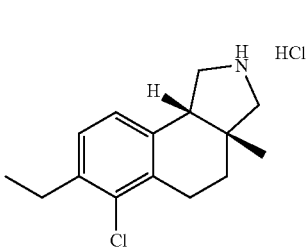 [SMILES: Cl ; CCc1ccc2c(c1Cl)CC[C@@]1(C)CNC[C@@H]21]

Similar protocols to procedures in example 7 (using cis-2-benzyl-6-chloro-3a-methyl-7-vinyl-2,3,3a,4,5,9b-hexahydro-1H-benzo[e]isoindole hydrochloride) were employed to afford cis-6-chloro-7-ethyl-3a-methyl-2,3,3a,4,5,9b-hexahydro-1H-benzo[e]isoindole hydrochloride, m/z=250.2 [M+H]⁺.

EXAMPLE 40 cis-6-Chloro-3a-methyl-7-((Z)-prop-1-enyl)-2,3,3a,4,5,9b-hexahydro-1H-benzo[e]isoindole hydrochloride

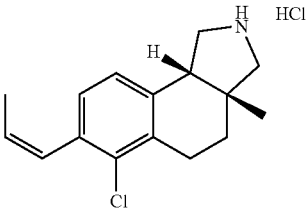 [SMILES: Cl ; C/C=C\c1ccc2c(c1Cl)CC[C@@]1(C)CNC[C@@H]21]

40.1 Preparation of cis-2-benzyl-6-chloro-3a-methyl-7-((Z)-prop-1-enyl)-2,3,3a,4,5,9b-hexahydro-1H-benzo[e]isoindole

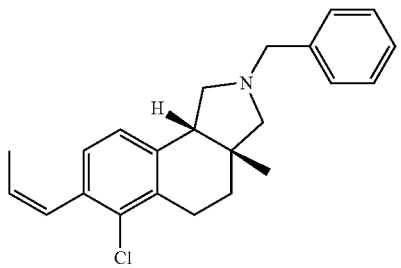 [SMILES: C/C=C\c1ccc2c(c1Cl)CC[C@@]1(C)CN(Cc3ccccc3)C[C@@H]21]

Similar protocols to procedures in example 5 (using cis-2-benzyl-7-bromo-6-chloro-3a-methyl-2,3,3a,4,5,9b-hexahydro-1H-benzo[e]isoindole) were employed to afford cis-2-benzyl-6-chloro-3a-methyl-7-((Z)-prop-1-enyl)-2,3,3a,4,5,9b-hexahydro-1H-benzo[e]isoindole, m/z=352.2 [M+H]⁺.

40.2 cis-6-Chloro-3a-methyl-7-((Z)-prop-1-enyl)-2,3,3a,4,5,9b-hexahydro-1H-benzo[e]isoindole hydrochloride

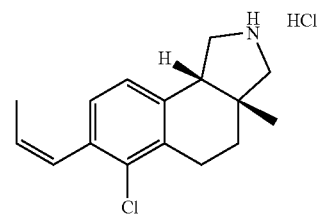 [SMILES: Cl ; C/C=C\c1ccc2c(c1Cl)CC[C@@]1(C)CNC[C@@H]21]

Similar protocols to procedures in example 19 (using afford cis-2-benzyl-6-chloro-3a-methyl-7-((Z)-prop-1-enyl)-2,3,3a,4,5,9b-hexahydro-1H-benzo[e]isoindole) were employed to afford cis-6-chloro-3a-methyl-7-((Z)-prop-1-enyl)-2,3,3a,4,5,9b-hexahydro-1H-benzo[e]isoindole hydrochloride, m/z=262.0, 264.0 [M+H]⁺.

EXAMPLE 41 cis-6-Chloro-3a-methyl-7-propyl-2,3,3a,4,5,9b-hexahydro-1H-benzo[e]isoindole hydrochloride

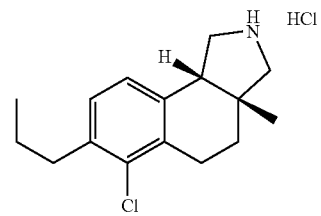

Similar protocols to procedures in example 7 (using cis-6-chloro-3a-methyl-7-((Z)-prop-1-enyl)-2,3,3a,4,5,9b-hexahydro-1H-benzo[e]isoindole) were employed to afford cis-6-chloro-3a-methyl-7-propyl-2,3,3a,4,5,9b-hexahydro-1H-benzo[e]isoindole hydrochloride, m/z=264.2 [M+H]⁺.

EXAMPLE 42 cis-7-Bromo-6-chloro-3a-methyl-2,3,3a,4,5,9b-hexahydro-1H-benzo[e]isoindole hydrochloride

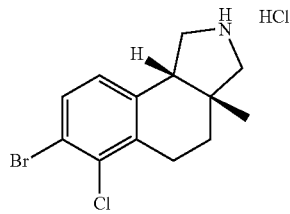 [SMILES: Cl ; C[C@@]12CCc3c(ccc(Br)c3Cl)[C@@H]1CNC2]

Similar protocols to procedures in example 11 (using cis-2-benzyl-7-bromo-6-chloro-3a-methyl-2,3,3a,4,5,9b-hexahydro-1H-benzo[e]isoindole) were employed to afford cis-7-bromo-6-chloro-3a-methyl-2,3,3a,4,5,9b-hexahydro-1H-benzo[e]isoindole hydrochloride, m/z=300.0, 302.0 [M+H]⁺.

EXAMPLE 43 trans-7-Bromo-6-chloro-3a-methyl-2,3,3a,4,5,9b-hexahydro-1H-benzo[e]isoindole hydrochloride

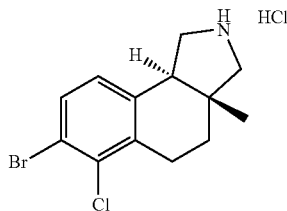 [SMILES: Cl ; C[C@@]12CCc3c(ccc(Br)c3Cl)[C@H]1CNC2]

Similar protocols to procedures in example 11 (using trans-2-benzyl-7-bromo-6-chloro-3a-methyl-2,3,3a,4,5,9b-hexahydro-1H-benzo[e]isoindole) were employed to afford trans-7-bromo-6-chloro-3a-methyl-2,3,3a,4,5,9b-hexahydro-1H-benzo[e]isoindole hydrochloride, m/z=300.0, 302.0 [M+H]⁺.

EXAMPLE 44

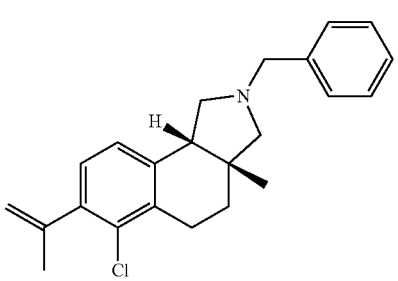 [SMILES: C=C(C)c1ccc2c(c1Cl)CC[C@@]1(C)CN(Cc3ccccc3)C[C@@H]21]

44.1 Preparation of cis-2-benzyl-6-chloro-3a-methyl-7-(prop-1-en-2-yl)-2,3,3a,4,5,9b-hexahydro-1H-benzo[e]isoindole Similar protocols to procedures in example 8 (using cis-2-benzyl-7-bromo-6-chloro-3a-methyl-2,3,3a,4,5,9b-hexahydro-1H-benzo[e]isoindole) were employed to afford cis-2-benzyl-6-chloro-3a-methyl-7-(prop-1-en-2-yl)-2,3,3a,4,5,9b-hexahydro-1H-benzo[e]isoindole, m/z=352.2 [M+H]⁺.

44.2 Preparation of cis-2-benzyl-6-chloro-7-isopropyl-3a-methyl-2,3,3a,4,5,9b-hexahydro-1H-benzo[e]isoindole

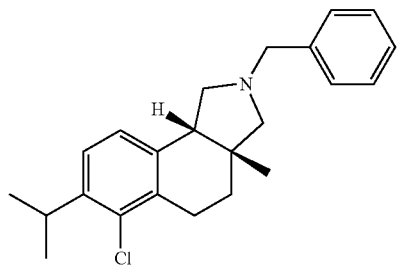 [SMILES: CC(C)c1ccc2c(c1Cl)CC[C@@]1(C)CN(Cc3ccccc3)C[C@@H]21]

A suspension of cis-2-benzyl-6-chloro-3a-methyl-7-(prop-1-en-2-yl)-2,3,3a,4,5,9b-hexahydro-1H-benzo[e]isoindole (0.156 mmol, 55 mg) and 5% Pd—C (7.81 μmol, 16.63 mg) in MeOH (3 ml) was stirred under H₂ atmosphere (1 bar, multiple hydrogenator) at ° C. for 1.5 h and then passed through Whatman membrane filter. The resulting filtrate was concentrated in vacuo a crude solid that was redissolved in MeOH (3 ml) and further 5% Pd—C (7.81 μmol, 16.63 mg) was added. The resulting suspension was stirred under H₂ atmosphere (balloon) at 20° C. for 3 h and then passed through Whatman membrane. The filtrate was concentrated to give cis-2-benzyl-6-chloro-7-isopropyl-3a-methyl-2,3,3a, 4,5,9b-hexahydro-1H-benzo[e]isoindole (46.6 mg), m/z=354.2 [M+H]⁺.

44.3 cis-6-Chloro-7-isopropyl-3a-methyl-2,3,3a,4,5,9b-hexahydro-1H-benzo[e]isoindole hydrochloride

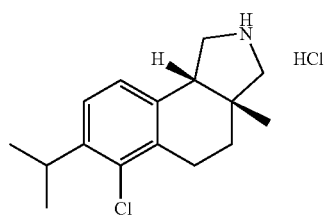 [SMILES: CC(C)c1ccc2c(c1Cl)CC[C@@]1(C)CNC[C@@H]21 ; Cl]

Similar protocols to procedures in example 11 (using cis-2-benzyl-6-chloro-7-isopropyl-3a-methyl-2,3,3a,4,5,9b-hexahydro-1H-benzo[e]isoindole) were employed to afford cis-6-chloro-7-isopropyl-3a-methyl-2,3,3a,4,5,9b-hexahydro-1H-benzo[e]isoindole hydrochloride, m/z=264.2 [M+H]⁺.

EXAMPLE 45

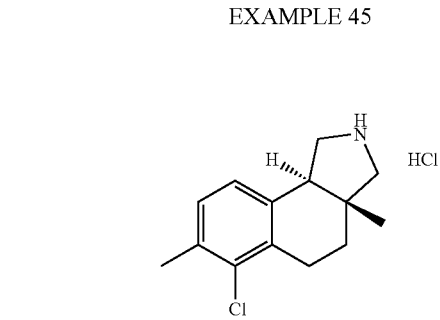

45.1 Preparation of trans-2-benzyl-6-chloro-3a,7-dimethyl-2,3,3a,4,5,9b-hexahydro-1H-benzo[e]isoindole

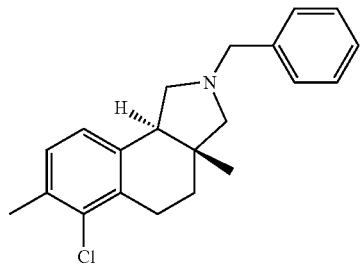

Similar protocols to procedures in example 33 (using trans-2-benzyl-6-chloro-7-bromo-3a-methyl-2,3,3a,4,5,9b-hexahydro-1H-benzo[e]isoindole) were employed to afford trans-2-benzyl-6-chloro-3a,7-dimethyl-2,3,3a,4,5,9b-hexahydro-1H-benzo[e]isoindole, m/z=326.2 [M+H]$^+$.

45.2 trans-6-Chloro-3a,7-dimethyl-2,3,3a,4,5,9b-hexahydro-1H-benzo[e]isoindole hydrochloride

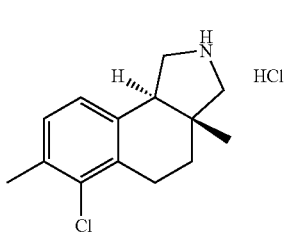

Similar protocols to procedures in example 11 (using trans-2-benzyl-6-chloro-3a,7-dimethyl-2,3,3a,4,5,9b-hexahydro-1H-benzo[e]isoindole) were employed to afford trans-6-chloro-3a,7-dimethyl-2,3,3a,4,5,9b-hexahydro-1H-benzo[e]isoindole hydrochloride, m/z=238.0, 240.0 [M+H]$^+$.

EXAMPLE 46

46.1 Preparation of trans-2-benzyl-6-chloro-7-cyclopropyl-3a-methyl-2,3,3a,4,5,9b-hexahydro-1H-benzo[e]isoindole

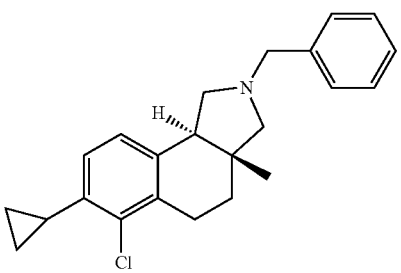

Similar protocols to procedures in example 10 (using trans-2-benzyl-6-chloro-7-bromo-3a-methyl-2,3,3a,4,5,9b-hexahydro-1H-benzo[e]isoindole) were employed to afford trans-2-benzyl-6-chloro-7-cyclopropyl-3a-methyl-2,3,3a,4,5,9b-hexahydro-1H-benzo[e]isoindole, m/z=352.2 [M+H]$^+$.

46.2 trans-6-Chloro-7-cyclopropyl-3a-methyl-2,3,3a,4,5,9b-hexahydro-1H-benzo[e]isoindole hydrochloride

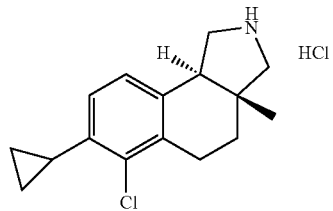 [SMILES: C[C@@]12CCc3c(ccc(C4CC4)c3Cl)[C@H]1CNC2 ; Cl]

Similar protocols to procedures in example 11 (using trans-2-benzyl-6-chloro-7-cyclopropyl-3a-methyl-2,3,3a,4,5,9b-hexahydro-1H-benzo[e]isoindole) were employed to afford trans-6-chloro-7-cyclopropyl-3a-methyl-2,3,3a,4,5,9b-hexahydro-1H-benzo[e]isoindole hydrochloride, m/z=262.0 [M+H]$^+$.

EXAMPLE 47 trans-6-Chloro-7-ethyl-3a-methyl-2,3,3a,4,5,9b-hexahydro-1H-benzo[e]isoindole hydrochloride

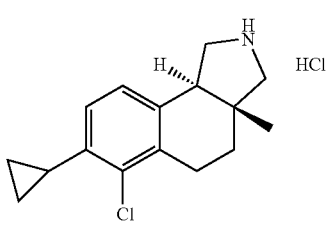 [SMILES: C[C@@]12CCc3c(ccc(C4CC4)c3Cl)[C@H]1CNC2 ; Cl]
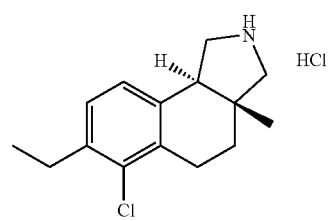 [SMILES: CCc1ccc2c(c1Cl)CC[C@@]1(C)CNC[C@H]21 ; Cl]

47.1 Preparation of trans-2-benzyl-6-chloro-7-ethyl-3a-methyl-2,3,3a,4,5,9b-hexahydro-1H-benzo[e]isoindole

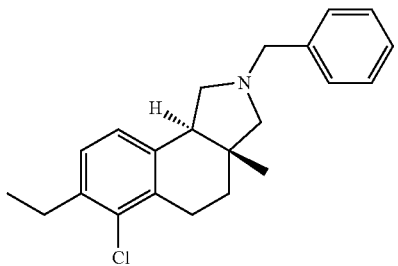 [SMILES: CCc1ccc2c(c1Cl)CC[C@@]1(C)CN(Cc3ccccc3)C[C@H]21]

A suspension of trans-2-benzyl-6-chloro-3a-methyl-7-vinyl-2,3,3a,4,5,9b-hexahydro-1H-benzo[e]isoindole (0.095 mmol, 32 mg) and 5% Pd—C (4.74 μmol, 10.08 mg) in MeOH (3 ml) was stirred under $H_2$ atmosphere (1 bar, multiple hydrogenator) at 20° C. for 1.5 h. The suspension was then passed through a Whatman membrane filter and the resulting filtrate was concentrated in vacuo to afford trans-2-benzyl-6-chloro-7-ethyl-3a-methyl-2,3,3a,4,5,9b-hexahydro-1H-benzo[e]isoindole (24.9 mg), m/z=340.2 $[M+H]^+$.

47.2 trans-6-Chloro-7-ethyl-3a-methyl-2,3,3a,4,5,9b-hexahydro-1H-benzo[e]isoindole hydrochloride

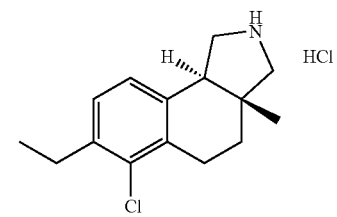 [SMILES: CCc1ccc2c(c1Cl)CC[C@@]1(C)CNC[C@H]21 ; Cl]

Similar protocols to procedures in example 11 (using trans-2-benzyl-6-chloro-7-ethyl-3a-methyl-2,3,3a,4,5,9b-hexahydro-1H-benzo[e]isoindole) were employed to afford trans-6-chloro-7-ethyl-3a-methyl-2,3,3a,4,5,9b-hexahydro-1H-benzo[e]isoindole hydrochloride, m/z=252.0 $[M+H]^+$.

EXAMPLE 48 trans-6-Chloro-3a-methyl-7-propyl-2,3,3a,4,5,9b-hexahydro-1H-benzo[e]isoindole hydrochloride

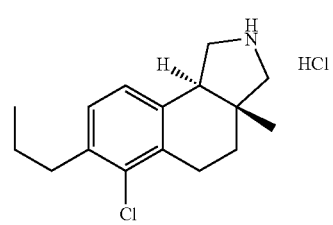 [SMILES: CCCc1ccc2c(c1Cl)CC[C@@]1(C)CNC[C@H]21 ; Cl]

Similar protocols to procedures in example 5-7 (using trans-2-benzyl-6-chloro-7-ethyl-3a-methyl-2,3,3a,4,5,9b-hexahydro-1H-benzo[e]isoindole and (Z)-prop-1-enylboronic acid) were employed to afford trans-6-chloro-7-ethyl-3a-methyl-2,3,3a,4,5,9b-hexahydro-1H-benzo[e]isoindole hydrochloride, m/z=264.2 $[M+H]^+$.

EXAMPLE 49 trans-6-Chloro-7-isopropyl-3a-methyl-2,3,3a,4,5,9b-hexahydro-1H-benzo[e]isoindole hydrochloride

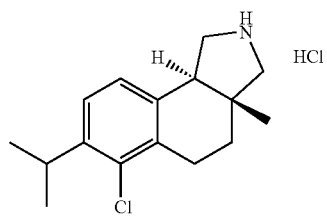 [SMILES: CC(C)c1ccc2c(c1Cl)CC[C@@]1(C)CNC[C@H]21 ; Cl]

Similar protocols to procedures in example 5-7 (using trans-2-benzyl-6-chloro-7-ethyl-3a-methyl-2,3,3a,4,5,9b-hexahydro-1H-benzo[e]isoindole and 4,4,5,5-tetramethyl-2-(prop-1-en-2-yl)-1,3,2-dioxaborolane) were employed to afford trans-6-chloro-7-isopropyl-3a-methyl-2,3,3a,4,5,9b-hexahydro-1H-benzo[e]isoindole hydrochloride, m/z=264.0 $[M+H]^+$.

EXAMPLE 50 trans-6-Chloro-7-methoxy-3a-methyl-2,3,3a,4,5,9b-hexahydro-1H-benzo[e]isoindole hydrochloride

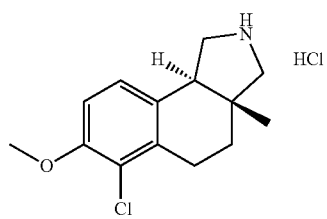

Similar protocols to procedures in example 11 (using trans-2-benzyl-6-chloro-7-methoxy-3a-methyl-2,3,3a,4,5,9b-hexahydro-1H-benzo[e]isoindole) were employed to afford trans-6-chloro-7-methoxy-3a-methyl-2,3,3a,4,5,9b-hexahydro-1H-benzo[e]isoindole hydrochloride, m/z=252.0 $[M+H]^+$.

EXAMPLE 51 trans-3a-Methyl-6-propyl-2,3,3a,4,5,9b-hexahydro-1H-benzo[e]isoindole hydrochloride

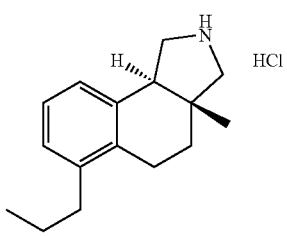 [SMILES: CCCc1cccc2c1CC[C@@]1(C)CNC[C@H]21 ; Cl]

Similar protocols to procedures in example 44 (using trans-2-benzyl-6-bromo-3a-methyl-2,3,3a,4,5,9b-hexahydro-1H-benzo[e]isoindole and (Z)-prop-1-enylboronic acid) were employed to afford trans-3a-methyl-6-propyl-2,3,3a,4,5,9b-hexahydro-1H-benzo[e]isoindole hydrochloride, m/z=244.3 [M+H]$^+$.

EXAMPLE 52

In Vitro Functional Assay

The aim of this assay is to identify compounds that act as agonists at the human 5-HT$_{2C}$ (VSV) receptor, stably expressed in CHO cells, using the Fluorescent Imaging Plate Reader (FLIPR; Molecular Devices).

All handling of genetically modified CHO cells are carried out under Class II containment following the GM (contained use) regulations 2000.

Cells maintained in UltraCHO Medium (Biowhittaker), supplemented with 1% dialysed fetal bovine serum (Hyclone) and 0.4 mg/ml Geneticin (GIBCO), at 37° C. with 5% CO$_2$ in air, and 90% humidity. Cells are split between 2-4 days growth. Passage conditions optimised to ensure that the cell density does not exceed 90% confluence. For all experiments cells are seeded at a density of 6×10$^5$/ml in plating medium (UltraCHO with 1% dialysed fetal bovine serum) then incubated at 37° C. with 5% CO$_2$ in air, and 90% humidity for 20-24 hours prior to the assay.

Media aspirated from cells and washed once with wash buffer (1×D-PBS —CaCl$_2$—MgCl$_2$) prior to incubation with Calcium-3 dye solution (containing 2.5 mM probenecid) for 1 hour at room temperature. Compounds added from drug plate to cell plate on FLIPR prior to fluorescence intensity reading.

Data analysed using in-house programme. Increase in measured relative fluorescence units (RFU) by test compound expressed as percentage maximal response of cells (evoked by 10 µM 5-HT). Concentration response curves constructed and analysed with appropriate non-linear regression 4 parameter logistic equation: y=A+((B−A)/(1+((C/x)^D))); where A=min Y, B=max Y, C=EC$_{50}$ and D=slope factor.

EXAMPLE 53

In-Vitro Radioligand Binding Assays

53.1 Saturation Binding Assays

Membrane homogenates from NIH-3T3 cells expressing human 5-HT$_{2C}$ (INI) receptors are prepared prior to saturation and competition binding experiments.

Using 96 deep well plates the following is added: 100 µl DMSO for total binding (1% final concentration), 100 µl mianserin for non-specific binding (NSB, 1 µM final concentration) and 100 µl appropriate radioligand concentration. Following 1.5 hour incubation at room temperature, reaction is terminated by vacuum filtration through a cell harvester onto a pre-soaked (0.03% PEI in assay buffer (Tris HCl, pH 7.4)) Whatman GF/B filter plate. Counts per minute (cpm) determined by scintillation counter. Protein concentration of membrane determined from standard curve of known concentration of bovine serum albumin (BSA); optical density read at 595 nm. Linear regression fitted to standard curve and calculation of membrane sample protein concentration performed using GraphPad Prism 4.0 or equivalent.

Using PRISM 4.0 or equivalent, free ligand concentration (nM) is plotted against the total, non-specific and specific binding. Non-linear regression and one site binding (hyperbola) are used for calculation of ligand concentration, K$_D$ (nM) and Bmax (pmol/mg protein) values:

$$y = \frac{B_{max} \cdot x}{(K_D + x)}$$

53.2 Competition Binding Assays

The aim of these assays are to determine binding efficiency of a compound using inhibition of [$^3$H] mesulergine (Amersham) binding to human 5-HT$_{2C}$ (INI) receptors expressed in NIH-3T3 cells as membrane homogenates.

Clozapine used as a reference; total binding determined by 1% DMSO; and non-specific binding determined by 10 µM clozapine. Assay format uses 96 deep-well microtitre plates in a total volume of 500 µl, such that each well contains 395 µl membrane, 5 µl test compound concentration or DMSO or clozapine, and 100 µl of appropriate concentration of radioligand. Following 1.5 hour incubation at room temperature, assay terminated by vacuum filtration through a cell harvester onto pre-soaked (0.03% PEI in assay buffer) Whatman GF/B filter plates. Radiation (cpm) counted using scintillation counter.

53.3 Data Analysis

Results are expressed relative to the maximal clozapine binding. Percentage effect is calculated for each well by correlating the cpm value with the mean of the values of the MIN wells (0%) and with the mean of the values of the MAX wells (100%) obtained from the same plate with the following formula:

$$\% \text{ Effect} = \frac{(\text{value} - \text{MIN})}{(\text{MAX} - \text{MIN})} \times 100\%$$

The individual effects at each concentration are used to fit the following four-parameter curve:

$$y = A + \frac{(B - A)}{\left(1 + \left(\frac{10^C}{x}\right)^D\right)}$$

Where A=min, B=max, C=inflection point (log$_{10}$ (EC$_{50}$)=−pEC$_{50}$) and D=hill slope.

Calculation of pKi, negative logarithm of the equilibrium dissociation constant, Ki $$Ki = \frac{EC50}{(1 + ([L]/K_D))}$$

Where EC$_{50}$=Concentration at point of inflection, [L]=radioligand concentration and K$_D$=equilibrium dissociation constant for the radioligand (expressed in the appropriate units of concentration).

Many of the above-noted compounds exhibited Ki values above 1 µM in this assay, whilst several others exhibited Ki values ranging from 1 µM to less than 500 nM.

EXAMPLE 54

Penile Erection/Head Shake Protocol

54.1 Introduction

Administration of 5-$HT_{2C}$ agonists induces penile erections in rats. This phenomenon is known to be mediated by 5-$HT_{2C}$ receptors since it can be reversed by treatment with a selective 5-$HT_{2C}$ antagonist. Activation of the 5-$HT_{2A}$ receptor induces head shakes, and this effect can be reversed by selective 5-$HT_{2A}$ antagonists. The test is used to evaluate a test compound for its activity at 5-$HT_{2C}$ and/or 5-$HT_{2A}$ receptors (Berendsen H H G, Jenck F, Broekkamp C L E. *Psychopharmacology* 1990, 101, 57-61).

54.2 Materials and Methods

Group housed male Wistar rats (Harlan Olac Ltd., Bicester, UK) weighing 200 g+ are housed in standard conditions with food and water ad-lib.

The test is carried out in a transparent perspex observation chamber (W: 10 cm, D: 10 cm, H: 20 cm). The test is videoed, 2 cameras are placed in front of the chambers and 2 below the chambers enabling all round observation of the rats.

Each experiment consists of a control group and n (usually 3) groups receiving test compound.

54.3 Procedure

Animals are habituated to the observation chambers on at least 3 occasions prior to the experiment.

On the day of the experiment each rat is weighed and identified (usually by tail marking). The test compound or vehicle is administered. Following the pre-treatment time the rats are placed individually into the observation chambers and video recording commences. PE and HS are usually recorded for 30 minutes.

PE and HS are considered to have occurred when the following behaviours are observed:

PE—An upright sitting position with repeated pelvic thrusts and an erect, engorged penis which the rat grooms.

HS—Sudden shaking of the head or whole body.

54.4 Evaluation of Responses

The mean number of PE and HS is calculated for each experimental group and statistical analysis is carried out using a one-way ANOVA followed by a Dunnetts test.

What is claimed is:

1. A tricyclic heterocyclic derivative according to Formula I

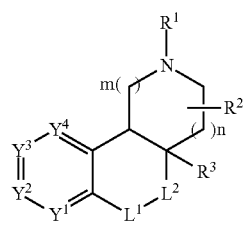

Formula I wherein
m is 1 and n is 0;

$R^1$ is H;

$R^2$ is H, $C_{3-5}$cycloalkyl or $C_{3-5}$cycloalkyl$C_{1-2}$alkyl said $C_{1-4}$alkyl, $C_{3-5}$cycloalkyl and $C_{3-5}$cycloalkyl$C_{1-2}$alkyl each being optionally substituted with one or more halogens;

$R^3$ is $C_{1-4}$alkyl, hydroxy$C_{1-2}$alkyl or $C_{1-2}$alkyloxy$C_{1-2}$alkyl said $C_{1-4}$alkyl and $C_{1-2}$alkyloxy$C_{1-2}$alkyl each being optionally substituted with one or more halogens;

$L^1$ is C=O or $CR^4R^5$;

$L^2$ is $CR^{4'}R^{5'}$;

$R^4$, $R^{4'}$, $R^5$ and $R^{5'}$ are each independently H, F, $C_{1-4}$alkyl, $C_{2-4}$alkenyl, $C_{2-4}$alkynyl, hydroxy, $C_{1-4}$alkyloxy, $C_{1-2}$alkyloxy$C_{1-2}$alkyl, $C_{3-5}$cycloalkyl or $C_{3-5}$cycloalkyl$C_{1-2}$alkyl said $C_{1-4}$alkyl, $C_{3-5}$cycloalkyl and $C_{3-5}$cycloalkyl$C_{1-2}$alkyl each being optionally substituted with one or more halogens or one of $R^4$ and $R^{4'}$ together with one of $R^5$ and $R^{5'}$ along with the atoms to which they are bonded form a 3-6 membered ring optionally comprising a heteroatom selected from O, S and $NR^{4''}$, wherein $R^{4''}$ is H, $C_{1-4}$alkyl, $COC_{1-4}$alkyl or $SO_2C_{1-4}$alkyl;

$Y^1$ is N or $CR^6$;

$Y^2$ is N or $CR^7$;

$Y^3$ is N or $CR^8$;

$Y^4$ is N or $CR^9$ with the proviso that no more than two of $Y^1$-$Y^4$ can be N simultaneously;

$R^6$ is H, $C_{1-6}$alkyl, $C_{2-6}$alkenyl, $C_{3-7}$cycloalkyl, or halogen, said $C_{1-6}$alkyl, and $C_{2-6}$alkenyl being optionally substituted with one or more halogens;

$R^7$ is H, $C_{1-6}$alkyl, $C_{3-7}$cycloalkyl, $C_{6-10}$aryl$C_{1-2}$alkyloxy or halogen, said $C_{1-6}$alkyl, and $C_{6-10}$aryl$C_{1-2}$alkyloxy being optionally substituted with one or more halogens;

$R^8$ is H, $C_{1-6}$alkyl, $C_{3-7}$cycloalkyl, $C_{6-10}$aryl$C_{1-2}$alkyloxy or halogen, said $C_{1-6}$alkyl, and $C_{6-10}$aryl$C_{1-2}$alkyloxy being optionally substituted with one or more halogens;

$R^9$ is H, with the proviso that $R^6$-$R^9$ cannot simultaneously be H;

$R^{10}$ and $R^{11}$ are each independently H or $C_{1-6}$alkyl; and $R^{12}$ is $C_{1-6}$alkyl;

or a pharmaceutically acceptable salt thereof.

2. The tricyclic heterocyclic derivative according to claim 1, wherein $R^2$ is H.

3. The tricyclic heterocyclic derivative according to claim 1, wherein $R^3$ is methyl, ethyl, fluoromethyl, hydroxymethyl, difluoromethyl or trifluoromethyl.

4. The tricyclic heterocyclic derivative according to claim 1, wherein $L^1$ is $CH_2$ and $L^2$ is $CH_2$.

5. The tricyclic heterocyclic derivative according to claim 1, wherein $Y^1$ is $CR^6$, $Y^2$ is $CR^7$, $Y^3$ is $CR^8$ and $Y^4$ is $CR^9$.

6. The tricyclic heterocyclic derivative according to claim 1, wherein $R^6$ is H, F, difluoromethyl, trifluoromethyl, chloro, bromo, cyclopropyl or 2-methylpropyl.

7. The tricyclic heterocyclic derivative according to claim 1, wherein $R^7$ is H, methyl, trifluoromethyl, ethyl, propyl, cyclopropyl, 2-methylpropyl, bromo or chloro.

8. The tricyclic heterocyclic derivative according to claim 1, wherein $R^8$ is H, methyl, trifluoromethyl, ethyl, or cyclopropyl.

9. A tricyclic heterocyclic derivative selected from:
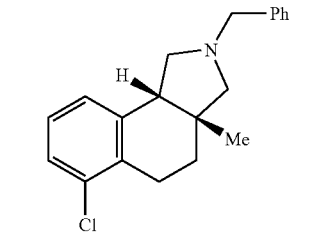
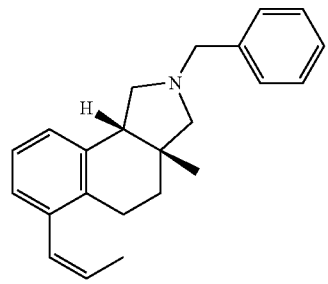
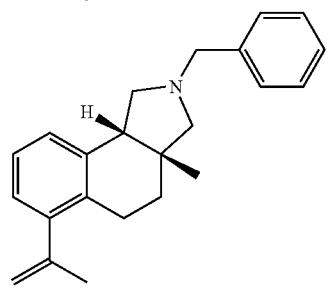
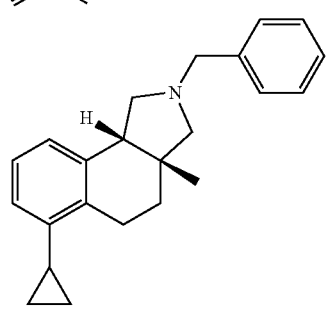
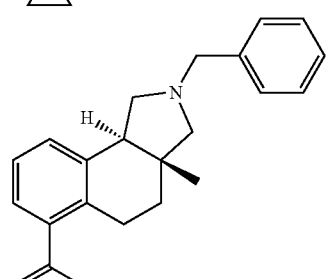
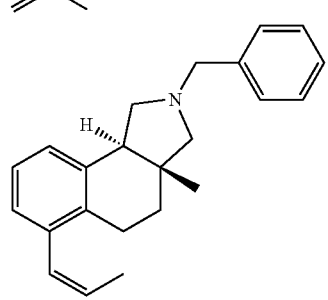
-continued
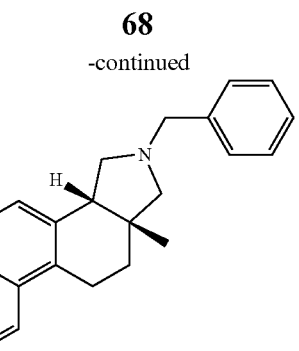
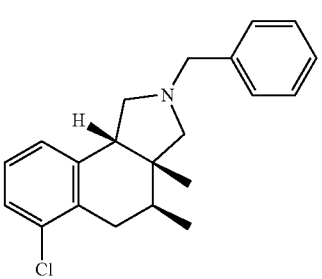
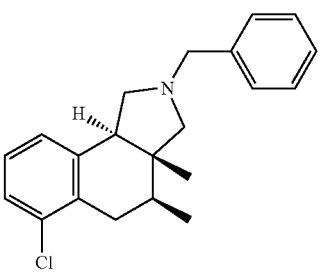
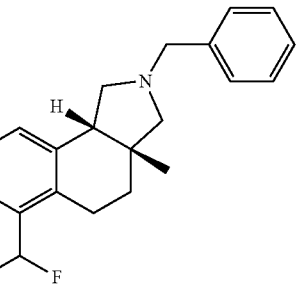
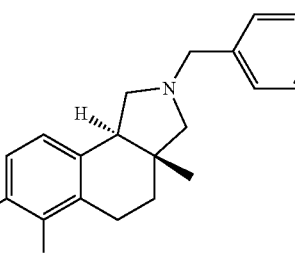
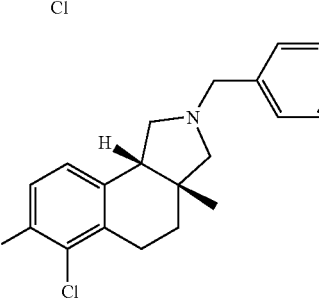

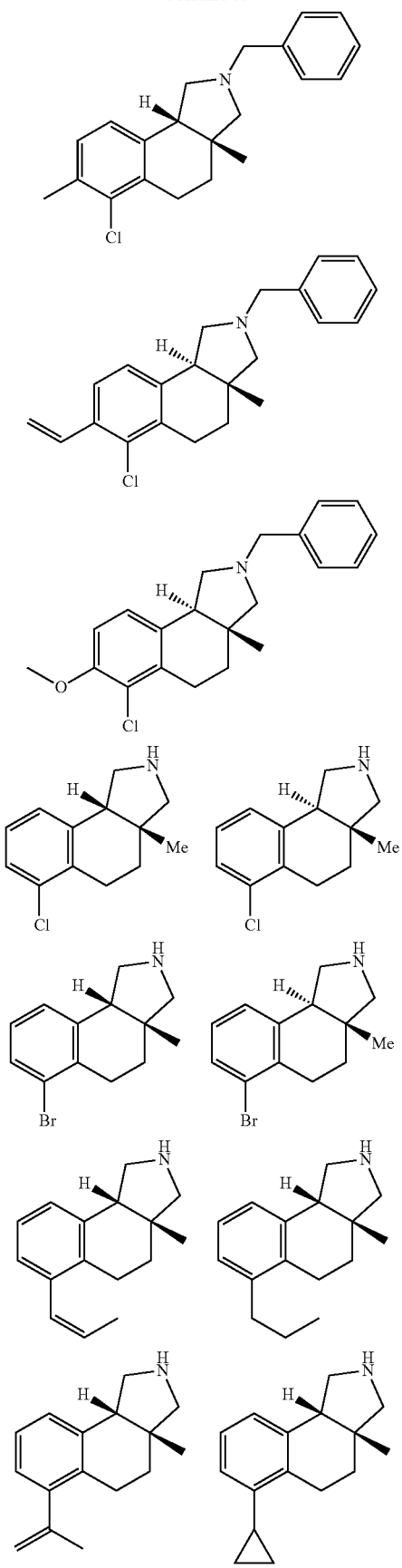
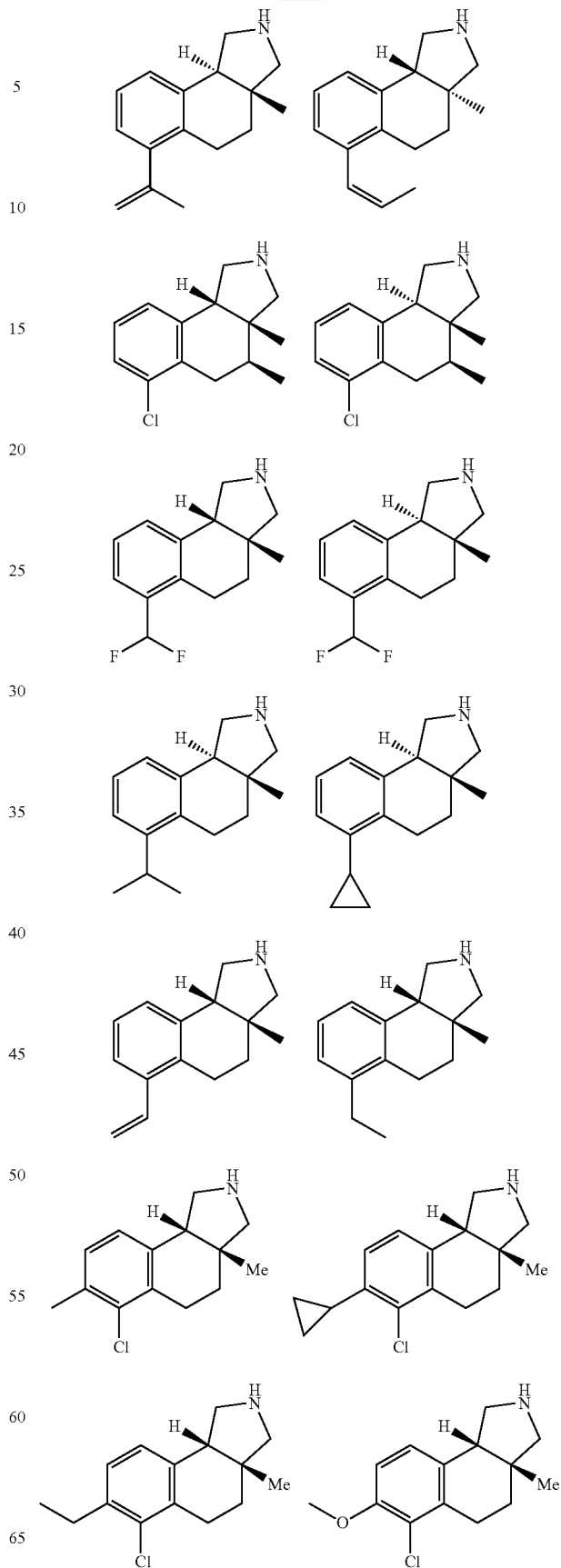

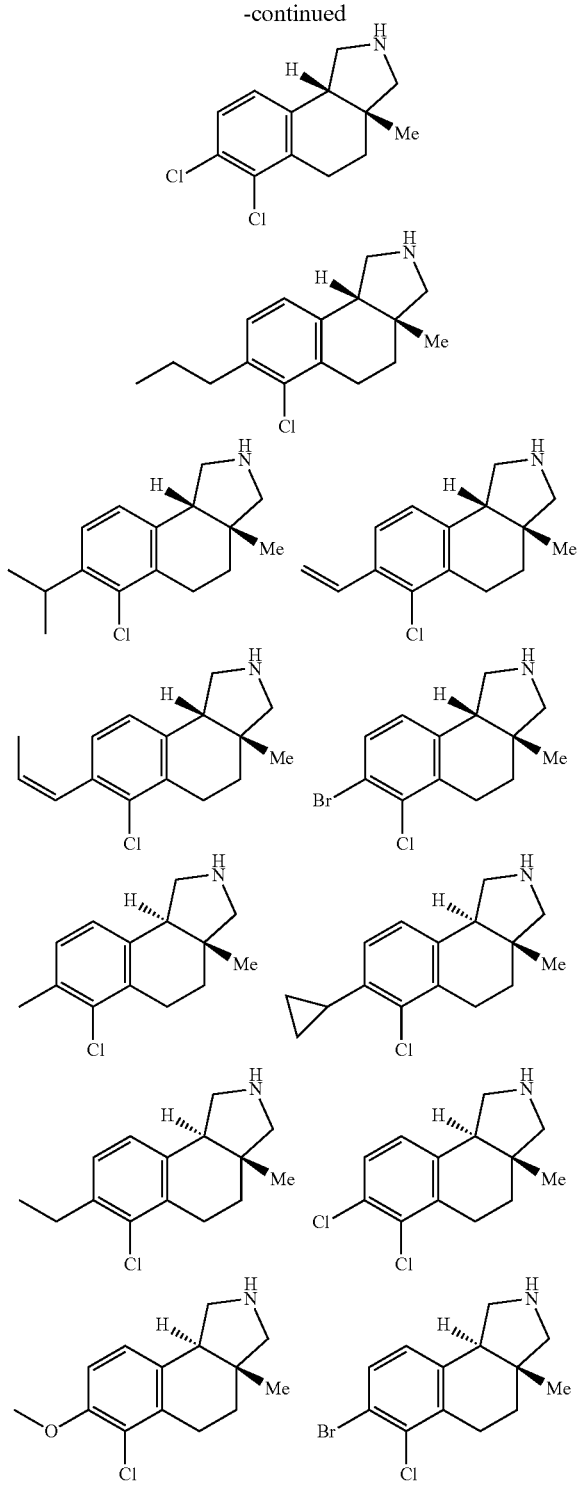
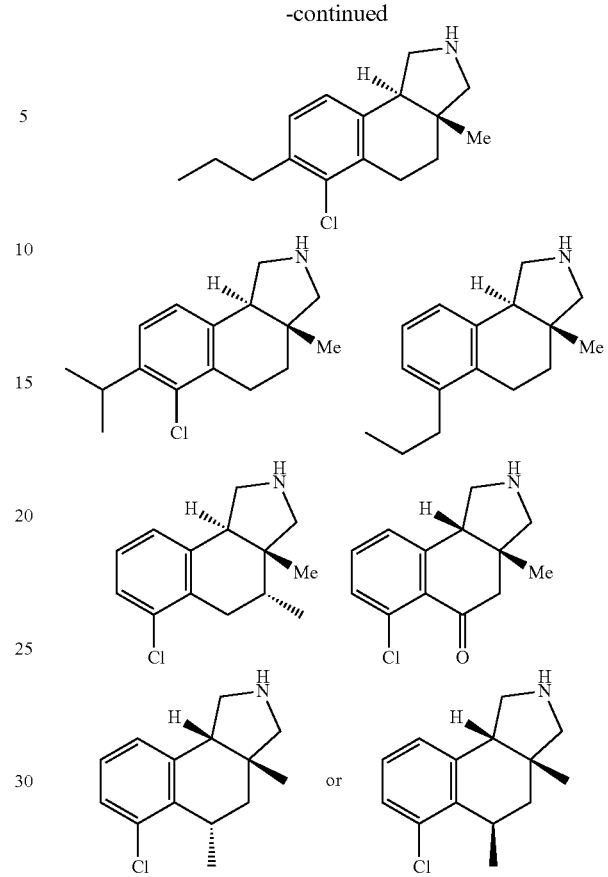

or a pharmaceutically acceptable salt.

10. A pharmaceutical composition comprising a tricyclic heterocyclic derivative according to claim 1 or a pharmaceutically acceptable salt thereof in admixture with one or more pharmaceutically acceptable excipient.

11. A pharmaceutical composition comprising a tricyclic heterocyclic derivative according to claim 9 or a pharmaceutically acceptable salt thereof in admixture with one or more pharmaceutically acceptable excipient.

12. A method of treating a serotonin mediated disorder, wherein the disorder is selected from the group consisting of obesity, diabetes (type I and type II), diabetic complications, atherosclerosis, impaired glucose tolerance and dyslipidemia, anxiety, depression, obsessive compulsive disorder, panic disorder, psychosis, schizophrenia, sleep disorder, sexual disorder and social phobias; cephalic pain; and migraine and gastrointestinal disorders, the method comprising administering to a patient in need thereof a therapeutically effective amount of a tricyclic heterocyclic derivative according to claim 1 or a pharmaceutically acceptable salt thereof.

* * * * *